US012781241B2

(12) United States Patent
Sallaud et al.

(10) Patent No.: US 12,781,241 B2
(45) Date of Patent: Nov. 3, 2026

(54) GPP(CRY)34-LIKE INSECTICIDAL PROTEINS

(71) Applicant: GENECTIVE SA, Saint-Beauzire (FR)

(72) Inventors: Christophe Sallaud, Chappes (FR); Laurent Décousset, Marsat (FR); Joseph Morrissey, Mahomet, IL (US)

(73) Assignee: GENECTIVE, Saint-Beauzire (FR)

( * ) Notice: Subject to any disclaimer, the term of this patent is extended or adjusted under 35 U.S.C. 154(b) by 0 days.

(21) Appl. No.: 18/874,930

(22) PCT Filed: Jun. 30, 2023

(86) PCT No.: PCT/EP2023/068108
§ 371 (c)(1),
(2) Date: Dec. 13, 2024

(87) PCT Pub. No.: WO2024/003392
PCT Pub. Date: Jan. 4, 2024

(65) Prior Publication Data

US 2025/0361523 A1 Nov. 27, 2025

Related U.S. Application Data

(60) Provisional application No. 63/367,397, filed on Jun. 30, 2022.

(30) Foreign Application Priority Data

Feb. 6, 2023 (EP) .................................... 23305155

(51) Int. Cl.
*C12N 15/82* (2006.01)
*C07K 14/32* (2006.01)

(52) U.S. Cl.
CPC .......... *C12N 15/8286* (2013.01); *C07K 14/32* (2013.01); *C12N 15/8205* (2013.01)

(58) Field of Classification Search
CPC . C12N 15/8286; C12N 15/8205; C07K 14/32
See application file for complete search history.

(56) References Cited

U.S. PATENT DOCUMENTS

| | | | |
|---|---|---|---|
| 5,188,960 | A | 2/1993 | Payne et al. |
| 5,605,793 | A | 2/1997 | Stemmer |
| 5,837,458 | A | 11/1998 | Minshull et al. |
| 5,880,275 | A | 3/1999 | Fischhoff et al. |
| 6,033,874 | A | 3/2000 | Baum et al. |
| 6,048,838 | A | 4/2000 | Ensign et al. |
| 6,083,499 | A | 7/2000 | Narva et al. |
| 6,127,180 | A | 10/2000 | Narva et al. |
| 6,218,188 | B1 | 4/2001 | Cardineau et al. |
| 6,248,535 | B1 | 6/2001 | Danenberg et al. |
| 6,326,351 | B1 | 12/2001 | Donovan et al. |
| 6,340,593 | B1 | 1/2002 | Cardineau et al. |
| 6,379,946 | B1 | 4/2002 | Ensign et al. |
| 6,399,330 | B1 | 6/2002 | Donovan et al. |
| 6,501,009 | B1 | 12/2002 | Romano |
| 6,548,291 | B1 | 4/2003 | Narva et al. |
| 6,624,145 | B1 | 9/2003 | Narva et al. |
| 6,713,063 | B1 | 3/2004 | Malvar et al. |
| 6,949,626 | B2 | 9/2005 | Donovan et al. |
| 6,962,705 | B2 | 11/2005 | Malvar et al. |
| 7,064,249 | B2 | 6/2006 | Corbin et al. |
| 7,070,982 | B2 | 7/2006 | Malvar et al. |
| 7,105,332 | B2 | 9/2006 | Abad et al. |
| 7,208,474 | B2 | 4/2007 | Bermudez et al. |
| 7,329,736 | B2 | 2/2008 | Abad et al. |
| 7,339,092 | B2 | 3/2008 | Abad et al. |
| 7,378,499 | B2 | 5/2008 | Abad et al. |
| 7,385,107 | B2 | 6/2008 | Donovan et al. |
| 7,449,552 | B2 | 11/2008 | Abad et al. |
| 7,462,760 | B2 | 12/2008 | Abad et al. |
| 7,476,781 | B2 | 1/2009 | Abad et al. |
| 7,504,229 | B2 | 3/2009 | Donovan et al. |
| 7,510,878 | B2 | 3/2009 | Abad et al. |
| 7,772,465 | B2 | 8/2010 | Abad et al. |
| 7,803,943 | B2 | 9/2010 | Mao et al. |
| 7,812,129 | B1 | 10/2010 | Abad et al. |
| 7,858,849 | B2 | 12/2010 | Cerf et al. |
| 7,923,602 | B2 | 4/2011 | Carozzi et al. |

(Continued)

FOREIGN PATENT DOCUMENTS

| | | | |
|---|---|---|---|
| WO | 2004074462 | A2 | 9/2004 |
| WO | 2005038032 | A1 | 4/2005 |

(Continued)

OTHER PUBLICATIONS

US 8,476,226 B2, 07/2013, Lira et al. (withdrawn)
Safety of Genetically Engineered Foods: Approaches to Assessing Unintended Health Effects. National Academies Press (US), Ch. 2, Methods and Mechanisms for Genetic Manipulation of Plants, Animals, and Microorganisms. (Year: 2004).*
Bravo et al. Evolution of Bacillus thiringiensis Cry toxins insecticidal activity. Microbiol Biotechnology. 6, 7-26. (Year: 2012).*
Anonymous: aegerolysin family protein [Aneurinibacillus migulanus]—Protein—NCBI WP_052520572, Jan. 19, 2023. Retrieved from the Internet: URL:https://www.ncbi.nlm.nih.gov/protein/WP_052520572. Originally deposited Aug. 19, 2015. (Year: 2015).*
Crickmore et al. A structure-based nomenclature for Bacillus thringiensis and other bacteria-derived pesticidal proteins. Journal of Invertabrate Pathology. (Year: 2021).*

(Continued)

*Primary Examiner* — Bratislav Stankovic
*Assistant Examiner* — Emily K Johnson
(74) *Attorney, Agent, or Firm* — Byron Olsen; Michael Best & Friedrich LLP

(57) ABSTRACT

Disclosed are transformed plants, transformed plants, transformed plant tissues, transformed plant cells, and transformed plant seeds having a recombinant nucleic acid molecule encoding a polypeptide having pesticidal activity. Also disclosed are methods of protecting a plant from infection by a plant pathogen by transforming plants, plant tissues, plant cells, and plant seeds with a recombinant nucleic acid molecule encoding a polypeptide having pesticidal activity.

10 Claims, 9 Drawing Sheets

Specification includes a Sequence Listing.

(56) References Cited

U.S. PATENT DOCUMENTS

| | | | |
|---|---|---|---|
| 8,084,416 | B2 | 12/2011 | Sampson et al. |
| 8,236,757 | B2 | 8/2012 | Carozzi et al. |
| 8,252,872 | B2 | 8/2012 | Tournilhac et al. |
| 8,304,604 | B2 | 11/2012 | Lira et al. |
| 8,304,605 | B2 | 11/2012 | Lira et al. |
| 8,318,900 | B2 | 11/2012 | Sampson et al. |
| 8,319,019 | B2 | 11/2012 | Abad et al. |
| 8,334,431 | B2 | 12/2012 | Sampson et al. |
| 8,461,415 | B2 | 6/2013 | Sampson et al. |
| 8,461,421 | B2 | 6/2013 | Sampson et al. |
| 8,461,422 | B2 | 6/2013 | Lira et al. |
| 8,513,493 | B2 | 8/2013 | Baum et al. |
| 8,609,936 | B2 | 12/2013 | Baum et al. |
| 8,772,577 | B2 | 7/2014 | Abad et al. |
| 8,802,933 | B2 | 8/2014 | Abad et al. |
| 8,816,157 | B2 | 8/2014 | Schnepf |
| 8,878,007 | B2 | 11/2014 | Abad et al. |
| 8,933,299 | B2 | 1/2015 | Abad et al. |
| 9,000,261 | B2 | 4/2015 | Abad et al. |
| 9,403,881 | B2 | 8/2016 | Abad et al. |
| 9,404,121 | B2 | 8/2016 | Abad et al. |
| 9,475,847 | B2 | 10/2016 | Altier et al. |
| 9,512,187 | B2 | 12/2016 | Je et al. |
| 9,593,345 | B2 | 3/2017 | Yamamoto et al. |
| 9,688,730 | B2 | 6/2017 | Cerf et al. |
| 11,174,295 | B2 | 11/2021 | Gruver et al. |
| 11,739,344 | B2 | 8/2023 | Barry et al. |
| 11,825,843 | B2 | 11/2023 | Barry et al. |
| 2004/0197916 | A1 | 10/2004 | Carozzi et al. |
| 2004/0197917 | A1 | 10/2004 | Carozzi et al. |
| 2004/0210964 | A1 | 10/2004 | Carozzi et al. |
| 2004/0210965 | A1 | 10/2004 | Carozzi et al. |
| 2004/0216186 | A1 | 10/2004 | Carozzi et al. |
| 2004/0250311 | A1 | 12/2004 | Carozzi et al. |
| 2006/0112447 | A1 | 5/2006 | Bogdanova et al. |
| 2006/0191034 | A1 | 8/2006 | Baum et al. |
| 2007/0028327 | A1 | 2/2007 | Perez et al. |
| 2008/0172762 | A1 | 7/2008 | Cerf et al. |
| 2008/0295207 | A1 | 11/2008 | Baum et al. |
| 2009/0144852 | A1 | 6/2009 | Tomso et al. |
| 2009/0307795 | A1 | 12/2009 | Perez et al. |
| 2009/0313721 | A1 | 12/2009 | Abad et al. |
| 2010/0004176 | A1 | 1/2010 | Sampson et al. |
| 2010/0017914 | A1 | 1/2010 | Hart et al. |
| 2010/0077507 | A1 | 3/2010 | Abad et al. |
| 2010/0077508 | A1 | 3/2010 | Abad et al. |
| 2010/0137216 | A1 | 6/2010 | Carozzi et al. |
| 2010/0160231 | A1 | 6/2010 | Sampson et al. |
| 2010/0192256 | A1 | 7/2010 | Abad et al. |
| 2010/0197592 | A1 | 8/2010 | Heinrichs |
| 2010/0269221 | A1 | 10/2010 | Abad et al. |
| 2010/0298211 | A1 | 11/2010 | Carozzi et al. |
| 2010/0306876 | A1 | 12/2010 | Perez et al. |
| 2010/0317569 | A1 | 12/2010 | Lira et al. |
| 2010/0319092 | A1 | 12/2010 | Lira et al. |
| 2010/0319093 | A1 | 12/2010 | Lira et al. |
| 2011/0023184 | A1 | 1/2011 | Desai et al. |
| 2011/0030096 | A1 | 2/2011 | Sampson et al. |
| 2011/0055968 | A1 | 3/2011 | Cerf et al. |
| 2011/0064710 | A1 | 3/2011 | Benson et al. |
| 2011/0112013 | A1 | 5/2011 | Abad et al. |
| 2011/0154536 | A1 | 6/2011 | Abad et al. |
| 2011/0263488 | A1 | 10/2011 | Carozzi et al. |
| 2012/0011621 | A1 | 1/2012 | Perez et al. |
| 2012/0047606 | A1 | 2/2012 | Abad et al. |
| 2012/0117690 | A1 | 5/2012 | Cerf et al. |
| 2012/0167259 | A1 | 6/2012 | Liu et al. |
| 2012/0192310 | A1 | 7/2012 | Abad et al. |
| 2012/0210462 | A1 | 8/2012 | Bermudez et al. |
| 2012/0233726 | A1 | 9/2012 | Abad et al. |
| 2012/0278954 | A1 | 11/2012 | Bowen et al. |
| 2013/0024998 | A1 | 1/2013 | Paul et al. |
| 2013/0055469 | A1 | 2/2013 | Sampson et al. |
| 2013/0097735 | A1 | 4/2013 | Bowen et al. |
| 2013/0104259 | A1 | 4/2013 | Sampson et al. |
| 2013/0117884 | A1 | 5/2013 | Hargiss et al. |
| 2013/0167264 | A1 | 6/2013 | Sampson et al. |
| 2013/0219570 | A1 | 8/2013 | Lira et al. |
| 2013/0269060 | A1 | 10/2013 | Baum et al. |
| 2013/0303440 | A1 | 11/2013 | Sampson et al. |
| 2013/0310543 | A1 | 11/2013 | Sampson et al. |
| 2014/0007292 | A1 | 1/2014 | Cerf et al. |
| 2014/0033361 | A1 | 1/2014 | Altier et al. |
| 2014/0033363 | A1 | 1/2014 | Sampson |
| 2014/0196175 | A1 | 7/2014 | Sampson et al. |
| 2014/0223598 | A1 | 8/2014 | Sampson et al. |
| 2014/0223599 | A1 | 8/2014 | Sampson et al. |
| 2014/0245491 | A1 | 8/2014 | Sampson et al. |
| 2014/0298538 | A1 | 10/2014 | Heinrichs et al. |
| 2014/0366227 | A1 | 12/2014 | Gatehouse et al. |
| 2014/0373195 | A1 | 12/2014 | Sampson et al. |
| 2015/0007360 | A1 | 1/2015 | Paul et al. |
| 2016/0150795 | A1 | 6/2016 | Baum et al. |
| 2016/0177332 | A1 | 6/2016 | Thayer et al. |
| 2016/0186204 | A1 | 6/2016 | Liu et al. |
| 2016/0194364 | A1 | 7/2016 | Abad et al. |
| 2016/0347799 | A1 | 12/2016 | Barry et al. |
| 2016/0366891 | A1 | 12/2016 | Diehn et al. |
| 2017/0166921 | A1 | 6/2017 | Barry et al. |
| 2017/0233440 | A1 | 8/2017 | Barry et al. |
| 2017/0233759 | A1 | 8/2017 | Abad et al. |
| 2017/0240603 | A1 | 8/2017 | Abad et al. |
| 2020/0138038 | A1 | 5/2020 | Ashby et al. |
| 2024/0167050 | A1 | 5/2024 | Abad et al. |
| 2024/0240200 | A1* | 7/2024 | Kelly ................. C12N 15/8286 |

FOREIGN PATENT DOCUMENTS

| | | | |
|---|---|---|---|
| WO | 2005021585 | B1 | 8/2005 |
| WO | 2006083891 | A2 | 8/2006 |
| WO | 2006119457 | A1 | 11/2006 |
| WO | 2007027776 | A2 | 3/2007 |
| WO | 2011103247 | A2 | 8/2011 |
| WO | 2011103248 | A2 | 8/2011 |
| WO | 2012139004 | A2 | 10/2012 |
| WO | 2014008054 | A2 | 1/2014 |
| WO | 2016061197 | A1 | 4/2016 |
| WO | 2016114973 | A1 | 7/2016 |
| WO | 2017023486 | A1 | 2/2017 |
| WO | 2017105987 | A1 | 6/2017 |
| WO | 2017132188 | A1 | 8/2017 |
| WO | 2017180715 | A2 | 10/2017 |
| WO | 2017192560 | A1 | 11/2017 |
| WO | 2018005411 | A1 | 1/2018 |
| WO | 2018064407 | A1 | 4/2018 |
| WO | 2018075197 | A1 | 4/2018 |
| WO | 2018075350 | A1 | 4/2018 |
| WO | 2018111553 | A1 | 6/2018 |
| WO | 2018140859 | A2 | 8/2018 |
| WO | 2020183022 | A1 | 9/2020 |
| WO | 2022236060 | A1 | 11/2022 |
| WO | 2024003392 | A1 | 1/2024 |

OTHER PUBLICATIONS

Chae et al. eCry1Gb.1lg, A Novel Chimeric Cry Protein with High Efficacy against Multiple Fall Armyworm (*Spodoptera frugiperda*) Strains Resistant to Different GM Traits. 14, 852. (Year: 2022).*

Nivya, V. et al. Recalcitrance to transformation, a hindrance for genome editing of legumes. Front Genome Ed. 5:1247815. doi: 10.3389/fgeed.2023. (Year: 2023).*

Crickmore et al. A structure-based nomenclature for Bacillus thuringiensis and other bacteria-derived pesticidal proteins, 186: 107438. (Year: 2021).*

Bravo, et al., Microbial Biotechnology, 6(1):17-26. (Year: 2012).*

Shu C., et al. Characterization of Two Novel Bacillus thuringiensis Cry8 Toxins Reveal Differential Specificity of Protoxins or Activated Toxins against Chrysomeloidea Coleopteran Superfamily. Toxins (Basel). 12(10):642. doi: 10.3390/toxins12100642. (Year: 2020).*

(56) References Cited

OTHER PUBLICATIONS

Frame et al. Improved Agrobacterium-mediated transformation of three maize inbred lines using MS salts, Plant Cell Rep, 25, 1024-1034. (Year: 2006).*
Crameri, A., et al. "DNA shuffling of a family of genes from diverse species accelerates directed evolution." Nature 391.6664 (1998): 288-291.
Crameri, A., et al. "Molecular evolution of an arsenate detoxification pathway by DNA shuffling." Nature biotechnology 15.5 (1997): 436-438.
Crickmore et al., "Bacillus thuringiensis toxin nomenclature" (2011), version dated Aug. 19, 2020, available online at https://web.archive.org/web/20200819224235/http://www.lifesci.sussex.ac.uk/home/Neil_Crickmore/Bt/ (3 pages).
Crickmore, N., et al. "A structure-based nomenclature for Bacillus thuringiensis and other bacteria-derived pesticidal proteins." Journal of invertebrate pathology 186 (2021): 107438.
Database Cas, Jan. 16, 2024, Sallaud Christophe et al., Database Accession No. CAS:2024_22125_3024848710_1 (1 page).
De Maagd, R. A., et al. "Domain III substitution in Bacillus thuringiensis delta-endotoxin CrylA (b) results in superior toxicity for Spodoptera exigua and altered membrane protein recognition." Applied and environmental microbiology 62.5 (1996): 1537-1543.
Ge, A. Z., et al. "Functional domains of Bacillus thuringiensis insecticidal crystal proteins. Refinement of Heliothis virescens and Trichoplusia ni specificity domains on CrylA (c)." Journal of Biological Chemistry 266.27 (1991): 17954-17958.
Hinchliffe, S. J., et al. "Insecticidal toxins from the Photorhabdus and Xenorhabdus bacteria." Open Toxinology Journal 3.2 (2010): 101-118.
International Search Report and Written Opinion for Application No. PCT/US2025/033810 dated Nov. 14, 2025 (21 pages).
Kapila, J., et al. "An Agrobacterium-mediated transient gene intact leaves." Plant Science 122.101 (1997): 101-108.
Li, D., et al. "Agrobacterium-mediated genetic transformation of Elymus breviaristatus with Pseudomonas pseudoalcaligenes insecticidal protein gene." Plant cell, tissue and organ culture 89.2 (2007): 159-168.
Liu, J.-R., et al. "Molecular cloning and characterization of an insecticidal toxin from Pseudomonas taiwanensis." Journal of agricultural and food chemistry 58.23 (2010): 12343-12349.
Ludwick, D. C., et al. "A new artificial diet for western corn rootworm larvae is compatible with and detects resistance to all current Bt toxins." Scientific reports 8.1 (2018): 5379.
Moore, J. C., et al. "Strategies for the in vitro evolution of protein function: enzyme evolution by random recombination of improved sequences." Journal of molecular biology 272.3 (1997): 336-347.
Morgan, J. A. W., et al. "Sequence analysis of insecticidal genes from Xenorhabdus nematophilus PMFI296." Applied and Environmental Microbiology 67.5 (2001): 2062-2069.
Naimov, S., et al. "Bacillus thuringiensis Delta-Endotoxin Cry1 Hybrid Proteins with Increased Activity against the Colorado Potato Beetle." Applied and Environmental Microbiology 67.11 (2001): 5328-5330.
Naimov, S., et al. "Solubilization, activation, and insecticidal activity of Bacillus thuringiensis serovar thompsoni HD542 crystal proteins." Applied and environmental microbiology 74.23 (2008): 7145-7151.
Opota, O., et al. "Monalysin, a novel ß-pore-forming toxin from the *Drosophila pathogen* Pseudomonas entomophila, contributes to host intestinal damage and lethality." PLoS pathogens 7.9 (2011): e1002259.
Péchy-Tarr, M., et al. "Molecular analysis of a novel gene cluster encoding an insect toxin in plant-associated strains of Pseudomonas fluorescens." Environmental microbiology 10.9 (2008): 2368-2386.
Pechy-Tarr. Pseudomonas protegens strain CHAO insecticidal toxin gene locus, complete sequence. GenBank Accession No. EU400157. Sep. 25, 2012 (12 pages).
Rang, Ce., et al. "Interaction between functional domains of Bacillus thuringiensis insecticidal crystal proteins." Applied and Environmental Microbiology 65.7 (1999): 2918-2925.
Schnepf, H. E., et al. "Specificity-determining regions of a lepidopteran-specific insecticidal protein produced by Bacillus thuringiensis." Journal of Biological Chemistry 265.34 (1990): 20923-20930.
Schöb, H., et al. "Silencing of transgenes introduced into leaves by agroinfiltration: a simple, rapid method for investigating sequence requirements for gene silencing." Molecular and General Genetics MGG 256.5 (1997): 581-585.
Stemmer, W. P. "DNA shuffling by random fragmentation and reassembly: in vitro recombination for molecular evolution." Proceedings of the National Academy of Sciences 91.22 (1994): 10747-10751.
Stemmer, WPC. "Rapid evolution of a protein in vitro by DNA shuffling." Nature 370.6488 (1994): 389-391.
Wang, K. et al. "Effective bacterial insecticidal proteins against coleopteran pests: A review." Archives of insect biochemistry and physiology 102.3 (2019): e21558.
Zhang, J., et al. "Cloning of the gene encoding an insecticidal protein in Pseudomonas pseudoalcaligenes." Annals of microbiology 59.1 (2009): 45-50.
Zhang, J.-H. et al. "Directed evolution of a fucosidase from a galactosidase by DNA shuffling and screening." Proceedings of the National Academy of Sciences 94.9 (1997): 4504-4509.
Anderson, O. D., et al. "Nucleotide sequences of the two high-molecular-weight glutenin genes from the D-genome of a hexaploid bread wheat, *Triticum aestivum* L. cv Cheyenne." Nucleic Acids Research 17.1 (1989): 461.
Anonymous: "Applications of aegerolysinlike proteins for detection and eradication of pests by Jaka Razinger | Research Project on ResearchGate", Sep. 30, 2016 (Sep. 30, 2016), Retrieved from the Internet: URL:http://researchgate.net/project/Applications-of-aegerolysinlike-proteins-for-detection-and-eradication-of-pests (3 pages).
Anonymous: aegerolysin family protein [Aneurinibacillus migulanus]—Protein—NCBI WP_052520572, Jan. 19, 2023. Retrieved from the Internet: URL:https://www.ncbi.nlm.nih.gov/protein/WP_052520572 (2 pages).
Frame, B.R., et al. (2006). Improved Agrobacterium-mediated transformation of three maize inbred lines using MS salts. Plant Cell Rep 25: 1024-1034.
Huynh MP, et al. (2017) Diet improvement for western corn rootworm (*Coleoptera: Chrysomelidae*) larvae. PLoS ONE 12 (11): e0187997. https//doi.org/10.1371/journal.pone.0187997.
International Preliminary Report on Patentability for Application No. PCT/EP2023/068108 dated Dec. 18, 2024 (7 pages).
International Search Report and Written Opinion for Application No. PCT/EP2023/068108 dated Aug. 29, 2023 (12 pages).
Karlin, S. et al. "Applications and statistics for multiple high-scoring segments in molecular sequences." Proceedings of the National Academy of Sciences 90.12 (1993): 5873-5877.
Karlin, S. et al. "Methods for assessing the statistical significance of molecular sequence features by using general scoring schemes." Proceedings of the National Academy of Sciences 87.6 (1990): 2264-2268.
Komari T, et al. (1996). Vectors carrying two separate T-DNAs for co-transformation of higher plants mediated by Agrobacterium tumefaciens and segregation of transformants free from selection markers. Plant J. 10:165-74.
Moar W., et al. (2017) Cry3Bb1-Resistant Western Corn Rootworm, Diabrotica virgifera virgifera (LeConte) Does Not Exhibit Cross-Resistance to DvSnf7 dsRNA, Plos One 12(1) (15 pages).
Myers, E.W. et al. "Optimal alignments in linear space." Bioinformatics 4.1 (1988): 11-17.
Needleman, S. B. et al. "A general method applicable to the search for similarities in the amino acid sequence of two proteins." Journal of molecular biology 48.3 (1970): 443-453.
Oleson JD, et al. Node-injury scale to evaluate root injury by corn rootworms (*Coleoptera: Chrysomelidae*). J Econ Entomol. Feb. 2005;98(1):1-8. doi: 10.1093/jee/98.1.1. PMID: 15765660.
Panevska, A., et al. "Effects of bioinsecticidal aegerolysin-based cytolytic complexes on non-target organisms." Toxins 13.7 (2021): 457.

(56) References Cited

OTHER PUBLICATIONS

Pearson, W. R. et al. "Improved tools for biological sequence comparison." Proceedings of the National Academy of Sciences 85.8 (1988): 2444-2448.
Pleau, H. et al. (2002) Development of an artificial diet for the western corn rootworm, Entomologia Experimentalis et Applicata, vol. 105, Issue1, pp. 1-11.
Robert, B., et al. "Hox-7, a mouse homeobox gene with a novel pattern of expression during embryogenesis." The EMBO journal 8.1 (1989): 91-100.
Sakurai, N., et al. "Cloning, expression, and pore-forming properties of mature and precursor forms of pleurotolysin, a sphingomyelin-specific two-component cytolysin from the edible mushroom Pleurotus ostreatus." Biochimica et Biophysica Acta (BBA)-Gene Structure and Expression 1679.1 (2004): 65-73.
Schünmann PHD, et al. (2003). A suite of novel promoters and terminators for plant biotechnology. Funct Plant Biol. 30:433-452.
Smith, T. F. et al. "Comparison of biosequences." Advances in applied mathematics 2.4 (1981): 482-489.
Verdaguer B, et al. (1996). Isolation and expression in transgenic tobacco and rice plants, of the cassava vein mosaic virus (CVMV) promoter. Plant Mol Biol. 31:1129-39.
Anonymous: "Uncharacterized protein—Aneurinibacillus migulanus (Bacillus migulanus) UniProtKB UniProt", , Dec. 4, 2017 (Dec. 4, 2017), XP093373633, Retrieved from the Internet: URL:https://www.uniprot.org/uniprotkb/A0A1G9C2C9/entry#function (3 pages).
European Patent Office. Office Action for Application No. 23736373.4, dated Mar. 12, 2026 (6 pages).

* cited by examiner

```
>Gpp34Aa1 and GUN0040A Alignment Alignment of 2 sequences: Gpp34Aa1, GUN0040A

Identities = 51/119 (42%),
Positives = 65/119 (54%), Gaps = 5/119 (4%)

(SEQ ID NO:2) Gpp34Aa1     1 MSAREVHIEINNKTRHTLQLEEKTKLSGGRWKTSPTNVARDTIKTFVAESRGFMTGVEGI  60
                               MSAREVHI + N +   LQLE KT L+ G W  +PTNV       F A+S GF TG EG
(SEQ ID NO:1) GUN0040A     1 MSAREVHITVINVSSFELQLESKTYLNHGEWILTPTNVPEGGRLNFRADSDGFAIGAEGS  60

(SEQ ID NO:2) Gpp34Aa1    61 IYFSVNGDAEISLRFDNPYIGSNWCDGSSDKPEYEVITQSGSGDKSHVTYTIQTVSLRL 119
                               I+++V  D EI L+FD+PY+GSN    ++  P   V     SG+   V Y I
(SEQ ID NO:1) GUN0040A    61 IFYTVP-DGEIKLYFDDPYVGSNAFRATTSSPSVSVQAVGSSGNVCKVKYVITNK---- 114
```

FIG. 1

| Specified Probability(Mortality) | Predicted Concentration ug/cm2 | Lower 95% | Upper 95% |
|---|---|---|---|
| 0.2500000 | 3.74759 | 1.97229 | 5.21225 |
| 0.5000000 | 6.51419 | 4.55580 | 9.04860 |
| 0.9000000 | 18.62406 | 12.42689 | 46.42862 |

Inverse Prediction

| Specified Probability(Dead) | Predicted Dose (ug/cm^2) | Lower 95% | Upper 95% |
|---|---|---|---|
| 0.2500000 | 3.0648 | 1.59427 | 5.250 |
| 0.5000000 | 12.4252 | 7.17331 | 26.390 |
| 0.9000000 | 177.5558 | 66.44738 | 1066.890 |

Expression Cassette Employed for GUN0040A Expression by E. coli.

Expression Cassette Employed for GN0040A Expression in plant.

Expression Cassette Employed for GUN0040A Expression in plant.

GPP(CRY)34-LIKE INSECTICIDAL PROTEINS

CROSS-REFERENCE TO RELATED APPLICATION(S)

This application is a U.S. national stage entry of International Patent Application No. PCT/EP2023/068108, filed on Jun. 30, 2023, which claims priority to European Patent Application No. 23305155.6, filed on Feb. 6, 2023, and U.S. Provisional Patent Application No. 63/367,397, filed on Jun. 30, 2022, the entire contents of each of which are fully incorporated herein by reference.

BACKGROUND OF THE DISCLOSURE

The present disclosure relates generally to compositions and methods for controlling pests. More particularly, the present disclosure provides compositions and methods for controlling plant pests.

Across the world, crops are subjected to multiple threats e.g. pests, plant diseases, weeds. Losses due to pests and diseases are greatly threatening global food supply hence the necessity to develop solutions to avoid partial or complete destruction of cultures. The main solutions are chemicals, biocontrols or GMO.

Current GMO strategies use genes expressing pesticidal proteins to produce transgenic crops. These pesticidal proteins are generally derived from *Bacillus thuringiensis*, a Gram-positive spore forming soil bacterium. They are called Cry (crystal protein) or VIP (Vegetative Insecticidal Protein). Transgenic crops expressing pesticidal proteins are used to combat crop damage from insects.

The wide adoption of *Bacillus* pesticidal proteins by farmers for controlling insects in the fields gave rise to resistance to these pesticidal proteins in some target pests in many parts of the world. One way of solving this problem is stacking genes encoding pesticidal proteins with different modes of action against insects in transgenic plants. In order to find new pesticidal proteins with new modes of action, the strategy consists in discovering new pesticidal proteins from other sources than *B. thuringiensis*. These new pesticidal proteins may be useful as alternatives to those derived from *B. thuringiensis* for deployment in pest-resistant transgenic plants.

While genetically engineering plants has been successful, pathogens can develop resistance over time. Accordingly, there exists a need to develop new proteins that can be expressed in plants to provide pathogen protection. To circumvent the resistance to commercial product over time, the new proteins can either display a different mode of action against the targets pest or display a higher toxicity against these target insects thus controlling insect populations that show resistance to less efficacious proteins.

BRIEF DESCRIPTION OF THE DISCLOSURE

The present disclosure is generally related to compositions and methods for controlling pests. More particularly, the present disclosure provides compositions and methods for controlling plant pests.

The compositions and methods disclosed herein are useful for pesticidal activity. Compositions include isolated, recombinant, and purified polypeptides having pesticidal activity. Recombinant nucleic acid molecules including DNA constructs and vectors encode polypeptides having pesticidal activity. Nucleic acid molecules and polypeptides are provided as DNA constructs and expression cassettes for transforming plants, plant tissues, plant cells, and plant seeds, as well as microorganisms.

In one aspect, the present disclosure is directed to a method of protecting a plant from infection by a plant pathogen, the method comprising: introducing to the plant a nucleic acid molecule encoding a polypeptide having at least 70% sequence identity to SEQ ID NO:1, wherein the plant expresses the nucleic acid molecule and wherein the polypeptide has pesticidal activity.

In one aspect, the present disclosure is directed to a transformed plant, transformed plant tissue, transformed plant cell, and transformed plant seed comprising a recombinant nucleic acid molecule encoding a polypeptide having at least 70% sequence identity to SEQ ID NO:1 stably incorporated into the transformed plant genome, the transformed plant tissue genome, the transformed plant cell genome, and the transformed plant seed genome, wherein the transformed plant, the transformed plant tissue, the transformed plant cell, and the transformed plant seed is capable of expressing the recombinant nucleic acid molecule, wherein the polypeptide has pesticidal activity.

In one aspect, the present disclosure is directed to a recombinant nucleic acid molecule comprising a nucleotide sequence encoding a polypeptide having at least 70% sequence identity to SEQ ID NO:1, wherein the polypeptide has pesticidal activity.

In one aspect, the present disclosure is directed to a vector comprising a recombinant nucleic acid molecule comprising a nucleotide sequence encoding a polypeptide having at least 70% sequence identity to SEQ ID NO:1, wherein the polypeptide has pesticidal activity.

In one aspect, the present disclosure is directed to a transformed host cell comprising a nucleic acid encoding a recombinant nucleic acid molecule comprising a nucleotide sequence encoding a polypeptide having at least 70% sequence identity to SEQ ID NO:1, wherein the polypeptide has pesticidal activity.

BRIEF DESCRIPTION OF THE DRAWINGS

The disclosure will be better understood, and features, aspects and advantages other than those set forth above will become apparent when consideration is given to the following detailed description thereof. Such detailed description makes reference to the following drawings, wherein:

FIG. 1 depicts a sequence alignment between GUN0040A amino acid sequence (SEQ ID NO:1) and Gpp34Aa1 (SEQ ID NO:2).

FIG. 6A depicts Western blot analysis using an anti-6×His tag antibody to detect 6×His tagged GUN0040A. Lanes 1 and 5 are 5 μg purified GUN0040A; Lane 2 is ProSc4::6×His::GUN0040A::terSbHSP co-infiltrated with ZsGreen::6×His; Lane 3 is ProCsVMV::IntOsActin::6×His::GUN0040A::terSbHSP; Lane 4 is proSc4::6×His::GUN0040A::terSbHSP. FIG. 6B is a photograph showing *Nicotiana benthamiana* infiltrated leaf discs exposed for 5 days to larvae in wells of 96-well plate.

FIG. 7A depicts the expression cassette employed for GUN0040A expression in *E. coli*. FIG. 7B depicts expression cassette proSc4::6×His::GUN0040A::SbHSP in construct used for expression in *N. benthamiana* transient expression assay. FIG. 7C depicts expression cassette proCsVMV::intOsActin::6×His::GUN0040A::SbHSP in construct used for expression in *N. benthamiana* transient expression assay.

DETAILED DESCRIPTION

Figure 2:
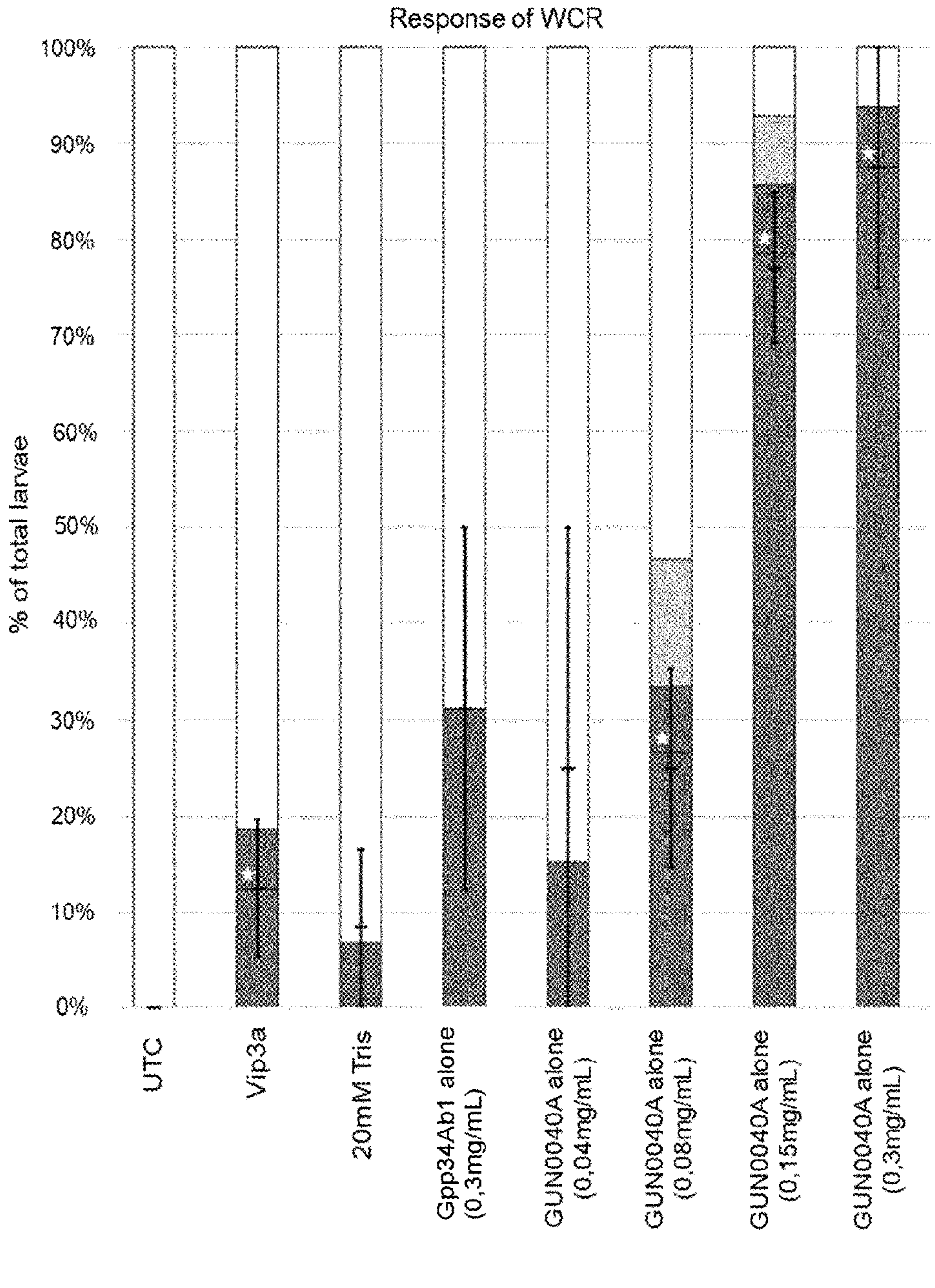
FIG. 2 is a graph depicting the activity of GUN0040A expressed in recombinant *E. coli* against Western Corn Root Worm (WCRW, *Diabrotica virgifera virgifera*) at concentrations ranging from 0.04 mg/mL to 0.3 mg/mL as compared to the activity of Gpp34Ab1 at 0.3 mg/mL. Untreated control (UTC) is a negative control only containing the insect diet, Vip3A is a negative control containing recombinant bacterial extract with Lepidopteran controlling toxin Vip3Aa19, and 20 mMTris is a negative control containing the buffer solution used for the purified proteins assays. Bars is % of mortality±SE.

Unless defined otherwise, all technical and scientific terms used herein have the same meaning as commonly understood by one of ordinary skill in the art to which the disclosure belongs. Although any methods and materials similar to or equivalent to those described herein can be used in the practice or testing of the present disclosure, the preferred methods and materials are described below.

The compositions and methods disclosed herein are useful for conferring pesticidal activity to plants. Compositions include isolated, recombinant, and purified polypeptides having pesticidal activity. Recombinant nucleic acid molecules including DNA constructs and vectors encode polypeptides having pesticidal activity. Nucleic acid molecules and polypeptides are provided as DNA constructs and expression cassettes for transforming plants, plant tissues, plant cells, and plant seeds, as well as microorganisms. Polypeptides having pesticidal activity disclosed herein provide useful alternatives to those derived from *B. thuringiensis* for deployment in transgenic plants.

As used herein, "pesticidal activity" means the proteins or polypeptides or toxin of the present disclosure is insecticidal and is able to induce the stunting (sub-lethal effect) and/or killing (lethal effect of insect pests).

In one aspect, the present disclosure is directed to an isolated nucleic acid encoding an amino acid sequence having at least 70% identity to SEQ ID NO:1, and having pesticidal activity. The pesticidal polypeptides and nucleic acid molecules encoding the pesticidal polypeptides of the present disclosure are particularly useful in agricultural crops for controlling and killing pests.

In one aspect, the present disclosure is directed to a method for producing a transgenic plant having pesticidal activity. The method includes transforming a plant cell with a nucleic acid encoding an amino acid having about 70% identity with SEQ ID NO:1, selecting a plant cell comprising the nucleic acid encoding the amino acid having about 70% identity with SEQ ID NO:1, and regenerating a transgenic plant from the plant cell comprising the nucleic acid encoding the amino acid having about 70% identity with SEQ ID NO:1, wherein the transgenic plant expresses the nucleic acid encoding the amino acid having about 70% identity with SEQ ID NO:1 and wherein the transgenic plant has pesticidal activity.

In one aspect, the present disclosure is directed to a method of protecting a plant from infection by a plant pathogen. The method includes: introducing to the plant a nucleic acid molecule encoding a polypeptide having at least 70% sequence identity to SEQ ID NO:1, wherein the plant expresses the nucleic acid molecule and wherein the polypeptide has pesticidal activity.

In one embodiment, the nucleic acid molecule encodes a polypeptide having at least 75% sequence identity to SEQ ID NO:1 and has pesticidal activity; in one embodiment, the nucleic acid molecule encodes a polypeptide having at least 80% sequence identity to SEQ ID NO:1 and has pesticidal activity; the nucleic acid molecule encodes a polypeptide having at least 85% sequence identity to SEQ ID NO:1 and has pesticidal activity; the nucleic acid molecule encodes a polypeptide having at least 90% sequence identity to SEQ ID NO:1 and has pesticidal activity; the nucleic acid molecule encodes a polypeptide having at least 91% sequence identity to SEQ ID NO:1 and has pesticidal activity; the nucleic acid molecule encodes a polypeptide having at least 92% sequence identity to SEQ ID NO:1 and has pesticidal activity; the nucleic acid molecule encodes a polypeptide having at least 93% sequence identity to SEQ ID NO:1 and has pesticidal activity; the nucleic acid molecule encodes a polypeptide having at least 94% sequence identity to SEQ ID NO:1 and has pesticidal activity; the nucleic acid molecule encodes a polypeptide having at least 95% sequence identity to SEQ ID NO:1 and has pesticidal activity; the nucleic acid molecule encodes a polypeptide having at least 96% sequence identity to SEQ ID NO:1 and has pesticidal activity; the nucleic acid molecule encodes a polypeptide having at least 97% sequence identity to SEQ ID NO:1 and has pesticidal activity; the nucleic acid molecule encodes a polypeptide having at least 98% sequence identity to SEQ ID NO:1 and has pesticidal activity; the nucleic acid molecule encodes a polypeptide having at least 99% sequence identity to SEQ ID NO:1 and has pesticidal activity.

Suitable plants include dicotyledons and monocotyledons. Suitable dicotyledons include dicotyledons such as tobacco, cotton, soybean, sunflower, rapeseed and monocotyledons such as wheat, maize, rice, barley, sorghum, and preferably maize.

The plant is protected from infection by plant pathogens such as Western Corn Rootworm (*Diabrotica virgifera virgifera* LeConte), Northern Corn Rootworm (*Diabrotica barbarberi* Smith & Lawrence)), and Southern Corn Rootworm (*Diabrotica undecimpunctata howardi* Barber).

Methods of the present disclosure include introducing and expressing in a plant cell, plant part or plant a nucleic acid molecule or construct as described herein. As used herein, "introducing" means presenting to the plant cell, plant part or plant, a nucleic acid molecule or construct in such a manner that it gains access to the interior of a cell of the plant. The methods do not depend on the particular method for introducing the nucleic acid molecule or nucleic acid construct into the plant cell, plant part or plant, only that it gains access to the interior of at least one cell of the plant or plant part. Methods of introducing nucleotide sequences, selecting transformants and regenerating whole plants, which may require routine modification in respect of a particular plant species, are well known in the art. The methods include, but are not limited to, stable transformation methods, transient transformation methods, virus-mediated methods and sexual breeding. As such, the nucleic acid molecule or construct can be carried episomally or integrated into the genome of the host cell.

As used herein, "stable transformation" means that the nucleic acid molecule or construct of interest introduced into the plant integrates into the genome of the plant and is capable of being inherited by the progeny thereof. As used herein, "transient transformation" means that the nucleic acid molecule or construct of interest introduced into the plant is not inherited by progeny.

In one aspect, the present disclosure is directed to a host cell comprising a nucleic acid encoding an amino acid having about 70% identity with SEQ ID NO:1. Suitable host cells include prokaryote host cells and eukaryote host cells.

Particularly suitable prokaryote host cells include Archaea and Bacteria. Particularly suitable eukaryotes host cells include plants and fungi. Suitable host cells include microbial cells such as *Trichoderma, Aspergillus, Neurospora, Humicola, Penicillium, Fusarium, Thermomonospora, Bacillus, Pseudomonas, Escherichia, Clostridium, Cellulomonas, Streptomyces, Yarrowia, Pichia* and *Saccharomyces*, and microalgal cell such as belonging to cyanobacterial species. Suitable plant host cells include dicotyledons and monocotyledons. Suitable dicotyledons include dicotyledons such as tobacco, cotton, soybean, sunflower, rapeseed and monocotyledons such as wheat, maize, rice, barley, sorghum, and preferably maize.

In one aspect, the present disclosure is directed to a transgenic plant, a transgenic plant tissue, a transgenic plant cell, and a transgenic plant seed comprising a nucleic acid encoding an amino acid having about 70% identity with SEQ ID NO:1 and having pesticidal activity.

In one embodiment, the nucleic acid molecule encodes a polypeptide having at least 75% sequence identity to SEQ ID NO:1 and has pesticidal activity; in one embodiment, the nucleic acid molecule encodes a polypeptide having at least 80% sequence identity to SEQ ID NO:1 and has pesticidal activity; the nucleic acid molecule encodes a polypeptide having at least 85% sequence identity to SEQ ID NO:1 and has pesticidal activity; the nucleic acid molecule encodes a polypeptide having at least 90% sequence identity to SEQ ID NO:1 and has pesticidal activity; the nucleic acid molecule encodes a polypeptide having at least 91% sequence identity to SEQ ID NO:1 and has pesticidal activity; the nucleic acid molecule encodes a polypeptide having at least 92% sequence identity to SEQ ID NO:1 and has pesticidal activity; the nucleic acid molecule encodes a polypeptide having at least 93% sequence identity to SEQ ID NO:1 and has pesticidal activity; the nucleic acid molecule encodes a polypeptide having at least 94% sequence identity to SEQ ID NO:1 and has pesticidal activity; the nucleic acid molecule encodes a polypeptide having at least 95% sequence identity to SEQ ID NO:1 and has pesticidal activity; the nucleic acid molecule encodes a polypeptide having at least 96% sequence identity to SEQ ID NO:1 and has pesticidal activity; the nucleic acid molecule encodes a polypeptide having at least 97% sequence identity to SEQ ID NO:1 and has pesticidal activity; the nucleic acid molecule encodes a polypeptide having at least 98% sequence identity to SEQ ID NO:1 and has pesticidal activity; the nucleic acid molecule encodes a polypeptide having at least 99% sequence identity to SEQ ID NO:1 and has pesticidal activity.

Suitable transgenic plants, transgenic plant tissues, transgenic plant cells, and transgenic plant seeds include dicotyledons and monocotyledons. Suitable dicotyledons include dicotyledons such as tobacco, cotton, soybean, sunflower, rapeseed and monocotyledons such as wheat, maize, rice, barley, and sorghum. A particularly suitable transgenic plant, transgenic plant tissue, transgenic plant cell, and transgenic plant seed is maize.

The transformed plant cells, plant parts or plants can have at least one nucleic acid molecule, nucleic acid construct, expression cassette or vector as described herein that encodes an amino acid at least 70% identity to SEQ ID NO:1, wherein the transformed plant cells, transformed plant parts, and transformed plants have pesticidal activity.

As used herein, "plant cell" or "plant cells" means a cell obtained from or found in seeds, suspension cultures, embryos, meristematic regions, callus tissue, leaves, roots, shoots, gametophytes, sporophytes, pollen and microspores. Plant cell also includes modified cells, such as protoplasts, obtained from the aforementioned tissues, as well as plant cell tissue cultures from which plants can be regenerated, plant calli and plant clumps. As used herein, "plant part" or "plant parts" means organs such as embryos, pollen, ovules, seeds, flowers, kernels, ears, cobs, leaves, husks, stalks, stems, roots, root tips, anthers, silk and the like. As used herein, "plant" or "plants" means whole plants and their progeny. Progeny, variants and mutants of the regenerated plants also are included, provided that they comprise the introduced nucleic acid molecule.

A nucleic acid molecule or construct as described above herein can be introduced into the plant cell, plant part or plant using a variety of transient transformation methods. Methods of transiently transforming plant cells, plant parts or plants include, but are not limited to, *Agrobacterium* infection, microinjection or particle bombardment. Likewise, the nucleic acid molecules or constructs as described herein can be introduced into the plant cell, plant part or plant by contacting it with a virus or viral nucleic acids.

Plant cells that have been transformed can be grown into plants by methods well known in the art. These plants then can be grown, and either pollinated with the same transformed strain or different strains, and the resulting progeny having the desired phenotypic characteristic identified. Two or more generations can be grown to ensure that expression of the desired phenotypic characteristic is stably maintained and inherited, and then seeds harvested to ensure expression of the desired phenotypic characteristic has been achieved.

As used herein, a "nucleic acid" sequence means a DNA or RNA sequence. The term encompasses sequences that include any of the known base analogues of DNA and RNA such as, but not limited to 4-acetylcytosine, 8-hydroxy-N6-methyladenosine, aziridinylcytosine, pseudoisocytosine, 5-(carboxyhydroxylmethyl) uracil, 5-fluorouracil, 5-bromouracil, 5-carboxymethylaminomethyl-2-thiouracil, 5-carboxymethylaminomethyluracil, dihydrouracil, inosine, N6-isopentenyladenine, 1-methyladenine, 1-methylpseudouracil, 1-methylguanine, 1-methylinosine, 2,2-dimethylguanine, 2-methyladenine, 2-methylguanine, 3-methylcytosine, 5-methylcytosine, N6-methyladenine, 7-methylguanine, 5-methylaminomethyluracil, 5-methoxyaminomethyl-2-thiouracil, beta-D-mannosylqueosine, 5'-methoxycarbonylmethyluracil, 5-methoxyuracil, 2-methylthio-N6-isopentenyladenine, uracil-5-oxyacetic acid methylester, uracil-5-oxyacetic acid, oxybutoxosine, pseudouracil, queosine, 2-thiocytosine, 5-methyl-2-thiouracil, 2-thiouracil, 4-thiouracil, 5-methyluracil, -uracil-5-oxyacetic acid methylester, uracil-5-oxyacetic acid, pseudouracil, queosine, 2-thiocytosine, and 2,6-diaminopurine.

As used herein, "recombinant," when used in connection with a nucleic acid molecule, means a molecule that has been created or modified through deliberate human intervention such as by genetic engineering. For example, a recombinant nucleic acid molecule is one having a nucleotide sequence that has been modified to include an artificial nucleotide sequence or to include some other nucleotide sequence that is not present within its native (non-recombinant) form.

Further, a recombinant nucleic acid molecule has a structure that is not identical to that of any naturally occurring nucleic acid molecule or to that of any fragment of a naturally occurring genomic nucleic acid molecule spanning more than one gene. A recombinant nucleic acid molecule also includes, without limitation, (a) a nucleic acid molecule having a sequence of a naturally occurring genomic or extrachromosomal nucleic acid molecule, but which is not flanked by the coding sequences that flank the sequence in its natural position; (b) a nucleic acid molecule incorporated into a construct, expression cassette or vector, or into a host cell's genome such that the resulting polynucleotide is not identical to any naturally occurring vector or genomic DNA; (c) a separate nucleic acid molecule such as a cDNA, a genomic fragment, a fragment produced by polymerase chain reaction (PCR) or a restriction fragment; and (d) a recombinant nucleic acid molecule having a nucleotide sequence that is part of a hybrid gene (i.e., a gene encoding a fusion protein). As such, a recombinant nucleic acid molecule can be modified (chemically or enzymatically) or unmodified DNA or RNA, whether fully or partially single-stranded or double-stranded or even triple-stranded.

In particular, the polypeptide designated herein as "GUN0040A" is a distantly-related Cry protein (see, FIG. 1). The Cry proteins (crystal proteins or δ-endotoxins) are particularly toxic to certain insect species and nematodes. The amino acid sequence of GUN0040A is about 40% identical to Gpp34Ab1. Gpp34Ab1 is a 14 kilo Dalton (kDa) protein member the Gpp34 (formerly known as Cry34) family. In the presence of Gpp35Ab1, Gpp34Ab1 exhibits insecticidal activity towards Western Corn Rootworm.

The isolated nucleic acid molecule of the present disclosure encodes an amino acid having at least 70% identity to SEQ ID NO:1 and having pesticidal activity. Preferably, the isolated nucleic acid encodes an amino acid having at least 75% identity to SEQ ID NO:1 and having pesticidal activity, at least 80% identity to SEQ ID NO:1 and having pesticidal activity, at least 85% identity to SEQ ID NO:1 and having pesticidal activity, at least 90% identity to SEQ ID NO:1 and having pesticidal activity, at least 91% identity to SEQ ID NO:1 and having pesticidal activity, at least 92% identity to SEQ ID NO:1 and having pesticidal activity, at least 93% identity to SEQ ID NO:1 and having pesticidal activity, at least 94% identity to SEQ ID NO:1 and having pesticidal activity, at least 95% identity to SEQ ID NO:1 and having pesticidal activity, at least 96% identity to SEQ ID NO:1 and having pesticidal activity, at least 97% identity to SEQ ID NO:1 and having pesticidal activity, at least 98% identity to SEQ ID NO:1 and having pesticidal activity, and at least 99% identity to SEQ ID NO:1 and having pesticidal activity.

The present disclosure also relates to homologues of GUN0040A (SEQ ID NO: 1) provided that the homologs retain insecticidal activity. Homolog sequences can be isolated from public or private collections and can also be prepared by various conventional methods, such as random mutagenesis, site-directed mutagenesis, gene synthesis or gene shuffling, based on all or a part of the peptide sequences presented in the present disclosure or using all or part of their coding nucleotide sequences. Such homologs include, for example, deletions, insertions, or substitutions of one or more residues in the amino acid sequence of the protein, or a combination thereof. A GUN0040A homolog is a protein with at least 70% sequence identity with SEQ ID NO: 1, preferably at least 73% of sequence identity, preferably at least 75% identity, preferably at least 80% sequence identity, preferably at least 85% sequence identity, preferably at least 90% sequence identity, preferably at least 91% sequence identity, preferably at least 92% sequence identity, preferably at least 93% sequence identity, preferably at least 94% sequence identity, preferably at least 95% sequence identity, preferably at least 96% sequence identity, preferably at least 97% sequence identity, preferably at least 98% sequence identity, preferably at least 99% sequence identity, preferably at least 99.2% sequence identity, preferably at least 99.5% sequence identity, preferably at least 99.8% sequence identity, preferably at least 99.9% sequence identity.

The isolated nucleic acid can further be operably linked to a promoter. Suitable promoters are known in the art. Suitable promoters can drive expression of the isolated nucleic acid in a bacterial cell, a yeast cell, and a plant cell. Suitable promoters include inducible promoters, constitutive promoters, tissue-specific promoters, developmentally regulated promoters, meiosis promoters, organelle-specific promoters, and the like. Promoters can be tissue specific promoters such as leaf-specific promoters, seed-specific promoters, root-specific promoters, and the like. Suitable tissue specific promoters are disclosed in Anderson & Greene, 1989, Robert et al., 1989, United States Patent Application Publication Nos. 20130024998, 20150007360, 20120011621, 20100306876, 20090307795, and 20070028327.

In addition to the full-length nucleotide sequence of a nucleic acid molecule encoding an amino acid of SEQ ID NO:1, it is intended that the nucleic acid molecule encoding SEQ ID NO:1 can be a fragment or variant thereof that encodes a polypeptide capable of pesticidal activity. For nucleotide sequences, "fragment" means a portion of a nucleotide sequence of a nucleic acid molecule, for example, a portion of the nucleotide sequence encoding SEQ ID NO:1. Fragments of a nucleotide sequence may retain the biological activity of the reference nucleic acid molecule. For example, less than the entire sequence disclosed in SEQ ID NO:1 can be used and will encode a protein that retains its pesticidal activity. Alternatively, fragments of a nucleotide sequence that can be used as hybridization probes and an amplification primer. Fragments used as hybridization probes or primers generally do not need to retain biological activity. Thus, fragments of the nucleic acid molecules can be at least about 10, 15, 20, 25, 50, 75, 100, 125, 150, 175, 200, 250, 300, 350, 400, 450, 500, 550, 600, 650, 700, 750, 800, 850 or 900 nucleotides, or up to the number of nucleotides present in a full-length nucleic acid molecule. A biologically active portion (fragment or variant) of the nucleic acid molecule can be prepared by isolating part of the sequence of the nucleic acid molecule, operably linking that fragment to a promoter, expressing the nucleotide sequence encoding the protein, and assessing the amount or activity of the protein.

For nucleotide sequences, "variant" means a substantially similar nucleotide sequence to a nucleotide sequence of a recombinant nucleic acid molecule as described herein, for example, a substantially similar nucleotide sequence encoding SEQ ID NO:1. For nucleotide sequences, a variant comprises a nucleotide sequence having deletions (i.e., truncations) at the 5' and/or 3' end, deletions and/or additions of one or more nucleotides at one or more internal sites compared to the nucleotide sequence of the recombinant nucleic acid molecules as described herein; and/or substitution of one or more nucleotides at one or more sites compared to the nucleotide sequence of the recombinant nucleic acid molecules described herein. One of skill in the art understands that variants are constructed in a manner to maintain the open reading frame.

Generally, variants of a nucleotide sequence of the recombinant nucleic acid molecules as described herein will have at least about 70%, 75%, 80%, 85%, 90%, 91%, 92%, 93%, 94%, 95%, 96%, 97%, 98%, 99% or more sequence identity to the nucleotide sequence of the recombinant nucleic acid molecules as determined by sequence alignment programs and parameters as described elsewhere herein.

Determining percent sequence identity between any two sequences can be accomplished using a mathematical algorithm. Non-limiting examples of such mathematical algorithms include, but are not limited to, the algorithm of Myers & Miller (1988) *CABIOS* 4:11-17; the local alignment algorithm of Smith et al. (1981) *Adv. Appl. Math.* 2:482-489; the global alignment algorithm of Needleman & Wunsch (1970) *J. Mol. Biol.* 48:443-453; the search-for-local alignment method of Pearson & Lipman (1988)*Proc. Natl. Acad. Sci. USA* 85:2444-2448; the algorithm of Karlin & Altschul (1990) *Proc. Natl. Acad. Sci. USA* 87:2264-2268, modified as in Karlin & Altschul (1993) *Proc. Natl. Acad. Sci. USA* 90:5873-5877.

As used herein, "operably linked" means that the elements of the expression cassette are configured so as to perform their usual function. Thus, control sequences (i.e., promoters) operably linked to a coding sequence are capable of effecting expression of the coding sequence. The control sequences need not be contiguous with the coding sequence, so long as they function to direct the expression thereof. Thus, for example, intervening untranslated, yet transcribed, sequences can be present between a promoter and a coding sequence, and the promoter sequence still can be considered "operably linked" to the coding sequence.

The nucleotide sequence encoding the SEQ ID NO:1 also can be stacked with nucleotide sequences encoding for agronomic traits such as male sterility, stalk strength, flowering time or transformation technology traits such as cell cycle regulation or gene targeting. These stacked combinations can be created by any method including cross breeding plants by any conventional or TopCross™ methodology (DuPont Specialty Grains; Des Moines, Iowa), zinc finger nucleases (ZFNs), transcription activator-like effector nucleases (TALENs), clustered regularly interspaced short palindromic repeats (CRISPR) and other genetic transformation. If the traits are stacked by genetically transforming the plants, the nucleotide sequences of interest can be combined at any time and in any order. For example, a transgenic plant comprising one or more desired traits can be used as the target to introduce further traits by subsequent transformation. The traits can be introduced simultaneously in a co-transformation protocol with the polynucleotides of interest provided by any combination of transformation cassettes. For example, if two sequences will be introduced, the two sequences can be contained in separate expression cassettes (trans) or contained on the same transformation cassette (cis). Expression of the sequences can be driven by the same promoter or by different promoters.

In one aspect, the present disclosure is directed to a vector comprising a nucleic acid encoding an amino acid having about 70% identity with SEQ ID NO:1.

In one embodiment, the nucleic acid molecule encodes a polypeptide having at least 75% sequence identity to SEQ ID NO:1 and has pesticidal activity; in one embodiment, the nucleic acid molecule encodes a polypeptide having at least 80% sequence identity to SEQ ID NO:1 and has pesticidal activity; the nucleic acid molecule encodes a polypeptide having at least 85% sequence identity to SEQ ID NO:1 and has pesticidal activity; the nucleic acid molecule encodes a polypeptide having at least 90% sequence identity to SEQ ID NO:1 and has pesticidal activity; the nucleic acid molecule encodes a polypeptide having at least 91% sequence identity to SEQ ID NO:1 and has pesticidal activity; the nucleic acid molecule encodes a polypeptide having at least 92% sequence identity to SEQ ID NO:1 and has pesticidal activity; the nucleic acid molecule encodes a polypeptide having at least 93% sequence identity to SEQ ID NO:1 and has pesticidal activity; the nucleic acid molecule encodes a polypeptide having at least 94% sequence identity to SEQ ID NO:1 and has pesticidal activity; the nucleic acid molecule encodes a polypeptide having at least 95% sequence identity to SEQ ID NO:1 and has pesticidal activity; the nucleic acid molecule encodes a polypeptide having at least 96% sequence identity to SEQ ID NO:1 and has pesticidal activity; the nucleic acid molecule encodes a polypeptide having at least 97% sequence identity to SEQ ID NO:1 and has pesticidal activity; the nucleic acid molecule encodes a polypeptide having at least 98% sequence identity to SEQ ID NO:1 and has pesticidal activity; the nucleic acid molecule encodes a polypeptide having at least 99% sequence identity to SEQ ID NO:1 and has pesticidal activity.

Suitable vectors are known in the art. Particularly suitable vectors include antibiotic resistance or thermostable antibiotic resistance, or coding for an enzyme that can complement an auxotrophy (natural, such as overcoming the absence of an indispensable amino acid, or engineered, such as URA3-deficient mutants where URA3 is necessary for uracil biosynthesis). Selectable markers include those conferring resistance to antibiotics such as kanamycin (nptll gene), hygromycin (aph IV) spectinomycin (aadA) and gentamycin (aac3 and aacC4) or resistance to herbicides such as glufosinate (bar or pat), dicamba (DMO) and glyphosate (aroA or EPSPS). Selectable markers that allow a direct visual identification of transformants can also be employed, for example, genes expressing a colored or fluorescent protein such as a luciferase or green fluorescent protein (GFP) or a gene expressing a beta-glucuronidase or uidA gene (GUS) for which various chromogenic substrates are known.

In one aspect, the present disclosure is directed to a formulation including a recombinant polypeptide having at least 70% sequence identity to SEQ ID NO:1 and having pesticidal activity. When applied to a plant, the recombinant polypeptide exhibits pesticidal activity.

In one embodiment, the nucleic acid molecule encodes a polypeptide having at least 75% sequence identity to SEQ ID NO:1 and has pesticidal activity; in one embodiment, the nucleic acid molecule encodes a polypeptide having at least 80% sequence identity to SEQ ID NO:1 and has pesticidal activity; the nucleic acid molecule encodes a polypeptide having at least 85% sequence identity to SEQ ID NO:1 and has pesticidal activity; the nucleic acid molecule encodes a polypeptide having at least 90% sequence identity to SEQ ID NO:1 and has pesticidal activity; the nucleic acid molecule encodes a polypeptide having at least 91% sequence identity to SEQ ID NO:1 and has pesticidal activity; the nucleic acid molecule encodes a polypeptide having at least 92% sequence identity to SEQ ID NO:1 and has pesticidal activity; the nucleic acid molecule encodes a polypeptide having at least 93% sequence identity to SEQ ID NO:1 and has pesticidal activity; the nucleic acid molecule encodes a polypeptide having at least 94% sequence identity to SEQ ID NO:1 and has pesticidal activity; the nucleic acid molecule encodes a polypeptide having at least 95% sequence identity to SEQ ID NO:1 and has pesticidal activity; the nucleic acid molecule encodes a polypeptide having at least 96% sequence identity to SEQ ID NO:1 and has pesticidal activity; the nucleic acid molecule encodes a polypeptide having at least 97% sequence identity to SEQ ID NO:1 and has pesticidal activity; the nucleic acid molecule encodes a polypeptide having at least 98% sequence identity to SEQ ID NO:1 and has pesticidal activity; the nucleic acid molecule encodes a polypeptide having at least 99% sequence identity to SEQ ID NO:1 and has pesticidal activity.

Formulations of the recombinant polypeptide with an acceptable carrier are in the form of a suspension, a solution, an emulsion, a dusting powder, a dispersible granule, a wettable powder, and an emulsifiable concentrate, an aerosol, an impregnated granule, an adjuvant, a coatable paste, encapsulations and combinations thereof.

Formulations can include surface-active agents, inert carriers, preservatives, humectants, feeding stimulants, attractants, encapsulating agents, binders, emulsifiers, dyes, UV protectants, buffers, flow agents, fertilizers, solvents, dispersants, wetting agents, tackifiers, micronutrient donors, and combinations thereof.

In one aspect, the present disclosure is directed to a formula including a transformed bacteria having a nucleic acid encoding a polypeptide having at least 70% sequence identity to SEQ ID NO:1 and having pesticidal activity. When applied to a plant, the transformed bacteria express the nucleic acid and the polypeptide exhibits pesticidal activity.

In one embodiment, the nucleic acid molecule encodes a polypeptide having at least 75% sequence identity to SEQ ID NO:1 and has pesticidal activity; in one embodiment, the nucleic acid molecule encodes a polypeptide having at least 80% sequence identity to SEQ ID NO:1 and has pesticidal activity; the nucleic acid molecule encodes a polypeptide having at least 85% sequence identity to SEQ ID NO:1 and has pesticidal activity; the nucleic acid molecule encodes a polypeptide having at least 90% sequence identity to SEQ ID NO:1 and has pesticidal activity; the nucleic acid molecule encodes a polypeptide having at least 91% sequence identity to SEQ ID NO:1 and has pesticidal activity; the nucleic acid molecule encodes a polypeptide having at least 92% sequence identity to SEQ ID NO:1 and has pesticidal activity; the nucleic acid molecule encodes a polypeptide having at least 93% sequence identity to SEQ ID NO:1 and has pesticidal activity; the nucleic acid molecule encodes a polypeptide having at least 94% sequence identity to SEQ ID NO:1 and has pesticidal activity; the nucleic acid molecule encodes a polypeptide having at least 95% sequence identity to SEQ ID NO:1 and has pesticidal activity; the nucleic acid molecule encodes a polypeptide having at least 96% sequence identity to SEQ ID NO:1 and has pesticidal activity; the nucleic acid molecule encodes a polypeptide having at least 97% sequence identity to SEQ ID NO:1 and has pesticidal activity; the nucleic acid molecule encodes a polypeptide having at least 98% sequence identity to SEQ ID NO:1 and has pesticidal activity; the nucleic acid molecule encodes a polypeptide having at least 99% sequence identity to SEQ ID NO:1 and has pesticidal activity.

The biological activity of interest of the formulation controls disease-causing plant pathogens. Such biological activity can be assayed by applying the formulation to a plant having a plant disease or at risk of developing a plant disease an effective amount of the formulation comprising the recombinant protein having at least 70% sequence identity to SEQ ID NO:1 and determining if the formulation controls a plant pathogen that causes the plant disease.

Formulations of the transformed bacterial having a nucleic acid encoding a polypeptide having at least 70% sequence identity to SEQ ID NO:1 with an acceptable carrier are in the form of a suspension, a solution, an emulsion, a dusting powder, a dispersible granule, a wettable powder, and an emulsifiable concentrate, an aerosol, an impregnated granule, an adjuvant, a coatable paste, encapsulations and combinations thereof.

In one embodiment, the nucleic acid molecule encodes a polypeptide having at least 75% sequence identity to SEQ ID NO:1 and has pesticidal activity; in one embodiment, the nucleic acid molecule encodes a polypeptide having at least 80% sequence identity to SEQ ID NO:1 and has pesticidal activity; the nucleic acid molecule encodes a polypeptide having at least 85% sequence identity to SEQ ID NO:1 and has pesticidal activity; the nucleic acid molecule encodes a polypeptide having at least 90% sequence identity to SEQ ID NO:1 and has pesticidal activity; the nucleic acid molecule encodes a polypeptide having at least 91% sequence identity to SEQ ID NO:1 and has pesticidal activity; the nucleic acid molecule encodes a polypeptide having at least 92% sequence identity to SEQ ID NO:1 and has pesticidal activity; the nucleic acid molecule encodes a polypeptide having at least 93% sequence identity to SEQ ID NO:1 and has pesticidal activity; the nucleic acid molecule encodes a polypeptide having at least 94% sequence identity to SEQ ID NO:1 and has pesticidal activity; the nucleic acid molecule encodes a polypeptide having at least 95% sequence identity to SEQ ID NO:1 and has pesticidal activity; the nucleic acid molecule encodes a polypeptide having at least 96% sequence identity to SEQ ID NO:1 and has pesticidal activity; the nucleic acid molecule encodes a polypeptide having at least 97% sequence identity to SEQ ID NO:1 and has pesticidal activity; the nucleic acid molecule encodes a polypeptide having at least 98% sequence identity to SEQ ID NO:1 and has pesticidal activity; the nucleic acid molecule encodes a polypeptide having at least 99% sequence identity to SEQ ID NO:1 and has pesticidal activity.

Formulations can include surface-active agents, inert carriers, preservatives, humectants, feeding stimulants, attractants, encapsulating agents, binders, emulsifiers, dyes, UV protectants, buffers, flow agents, fertilizers, solvents, dispersants, wetting agents, tackifiers, micronutrient donors, and combinations thereof.

Transformed bacteria having a nucleic acid encoding a polypeptide having at least 70% sequence identity to SEQ ID NO:1 in the same manner that *Bacillus thuringiensis* strains have been used as insecticidal sprays.

The biological activity of interest of the bacteria controls disease-causing plant pathogens. Such biological activity can be assayed by applying to a plant having a plant disease or at risk of developing a plant disease an effective amount of the formulation comprising the bacteria and determining if the sprayed bacteria composition controls a plant pathogen that causes the plant disease.

In one aspect, the present disclosure is directed to a method for protecting a plant from an insect pest. The method includes expressing in a plant or a plant cell thereof a nucleotide acid encoding a polypeptide comprising an amino acid sequence having at least 70% sequence identity to SEQ ID NO:1, wherein the nucleic acid encodes a polypeptide having pesticidal activity and is operably linked to a promoter capable of driving expression in the plant or cell.

EXAMPLES

Example 1

In this Example, the GUN0040A sequence was determined.

DNA samples were isolated from the bacteria *Aneurinibacillus migulanus* from a public unassembled WGS sequence collection. Protein samples were available through the UNIPROT (uniprot.org) protein world database and referenced as a component of UP000182836.

Predicted protein sequences corresponding to coding regions in sequenced genomes were aligned using BLASTP against Gpp34 protein sequence which has demonstrated insecticidal activity. Novel sequences with a query/subject coverage length of 50% aa or more, and an identity of 30% aa or more, in the protein aligned region, were potential candidate-genes. GUN0040A (SEQ ID NO:1) displayed a 42% identity with Gpp34Aa1 (SEQ ID NO:2)—FIG. 1.

Example 2

In this Example, cloning and expression of GUN0040A was performed.

Figure 7A:
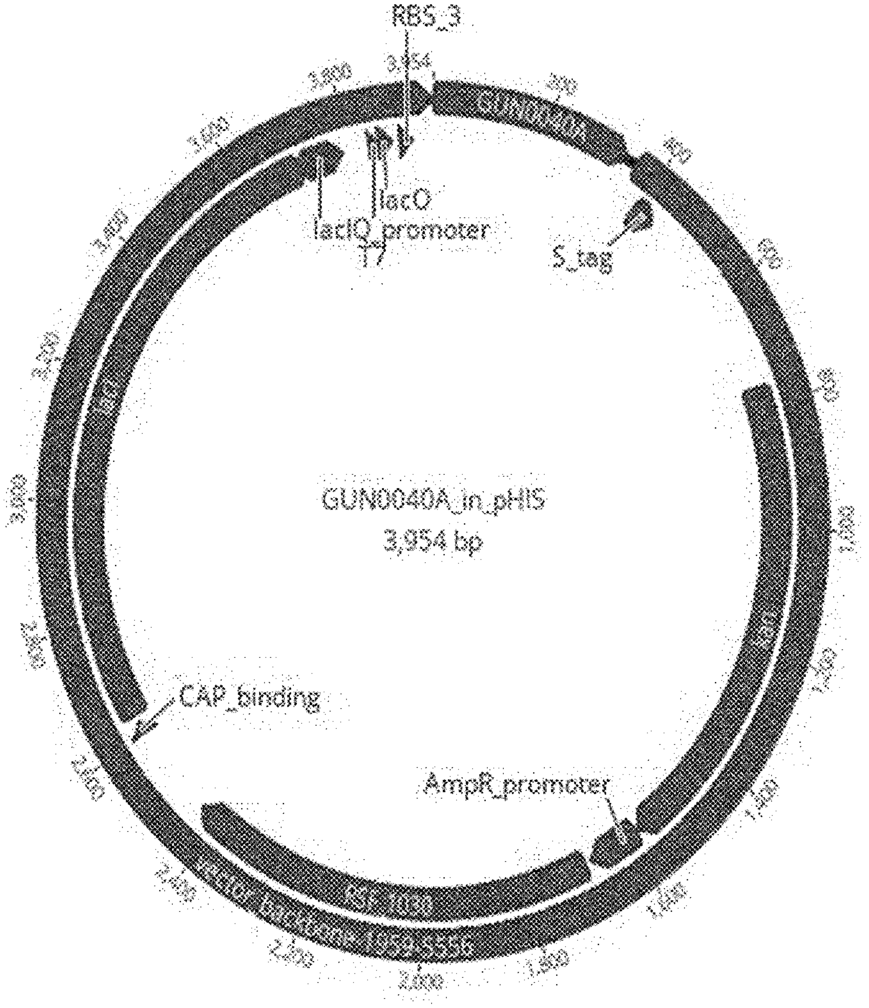
FIGS. 7A-7C depict constructs used for recombinant expression of GUN0040A.
Figure 7B:
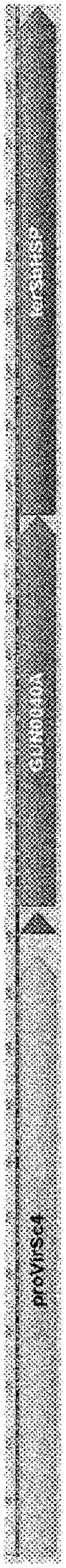

To express GUN0040A, the DNA gene coding sequence was optimized for expression in *E. coli*. This sequence was cloned into the pHis Expression Vector (modified version of pRSF-1b (Novagen)), thus fusing a N-terminal 6×His TAG coding sequence to GUN0040A gene (FIGS. 7A and 7B). The clone was transformed into *E. coli* strain BL21(DE3) and grown in an auto-induction medium (OVERNIGHT EXPRESS™ LB medium, EMD Millipore). Following induction, bacterial cells were harvested for recombinant protein purification prior to insect larval activity assay. In some cases, the bacterial culture following induction was used for insect assay.

Example 3

In this Example, insecticidal toxicity bioassays were conducted with transformed bacterial whole cells expressing GUN0040 protein to evaluate efficacy against the coleoptera species Western corn rootworm (WCR, *Diabrotica virgifera virgifera* LeConte).

Western corn rootworm specific artificial diet, WCRMO-1 (Huynh M P, et al., 2017), was used for larval feeding bioassays. Bacterial cultures were applied to the 0.32 $cm^2$ surface area of 200 μL semi-solid artificial diet in a 96-well microtiter plate following Pleau et al. (2002) and Moar et al. (2017). The treatments were air-dried in a biosafety hood. A similar volume of bacterial whole cells expressing an inactive protein, an active *Bacillus thuringiensis* (Bt) toxin and the bacterial growth media served as controls. One neonate larva of *D. virgifera* was placed into each well with a fine tipped paint brush. Larval mortality and/or stunting was recorded for each of the treatments at 5 days after infestation.

A transformant used as a negative control, as used in this example and the following ones, is a whole cell bacterial culture of *E. coli* produced under the same conditions and from the same bacterial strain containing the same expression vector as the treatments containing the insecticidal proteins with the exception that the expression vector either contains a known gene encoding a corn rootworm inactive protein.

After five days, whole cell bacterial cultures containing GUN0040 protein exhibited *D. virgifera* larval mortality and growth inhibition greater than the negative controls in bioassay (TABLE 1).

To explore the specificity of the insecticidal activity of GUN0040A protein, an artificial diet over-lay bioassay against a different insect family was carried out. Whole cell bacterial cultures prepared in the manner described above were tested against a lepidopteran crop pest, *Spodoptera frugiperda* (J. E. Smith) (Fall armyworm), *Helicoverpa zea* (Corn earworm), *Ostrinia nubilalis* (*European corn borer*) using a lepidopteran specific diet. GUN0040A protein did not exhibit elevated mortality or growth inhibition against any of the lepidopteranlarvae (*Spodoptera frugiperda, Helicoverpa zea* and *Ostrinia nubilalis*). (TABLE 1).

TABLE 1

Insecticidal activity of whole recombinant *E. coli* culture expressing either GUN0040A or coleopteran specific Gpp34Ab1/Gpp35Ab1, or Lepidopteran active Vip3Aa19

| Species tested | GUN0040A | Gpp34Ab1/Gpp35Ab1 | VIP3Aa19 |
|---|---|---|---|
| *Spodoptera frugiperda* | − | − | +++ |
| *Helicoverpa zea* | − | − | ++ |
| *Ostrinia nubilalis* | − | − | +++ |
| *Diabrotica virgifera virgifera* | +++ | +++ | − |

Example 4

In this Example, insecticidal activity of GUN0040 purified protein against susceptible *D. virgifera* populations was determined in an artificial diet-overlay bioassay.

An aliquot (20 μL) of protein solution, at increasing concentration, was applied to top of the diet (approximately 200 μL of WCRMO-1 diet/well of a standard 96-well microtiter plate), and subsequently dried in a laminar flow hood for approximately 30 minutes. Once dry, a single neonate WCRW larva was infested per well using a fine tipped watercolor brush. After larvae were infested, each plate was covered with a sealing film (Excel Scientific, Inc., Thermalseal RTS™, TSS-RTQ-100) and placed in a 25° C. dark growth chamber for 5 days. At day 5, each plate was removed from the growth chamber and larvae were assessed for mortality and stunted phenotypes (stunted depicted as the darkest shading with a star or slightly stunted depicted as the lightest shading; dead being depicted as the darkest shading with no star and unaffected being unshaded). Results showed a clear dose response of the GUN0040A protein alone (FIG. 2).

Figure 3:
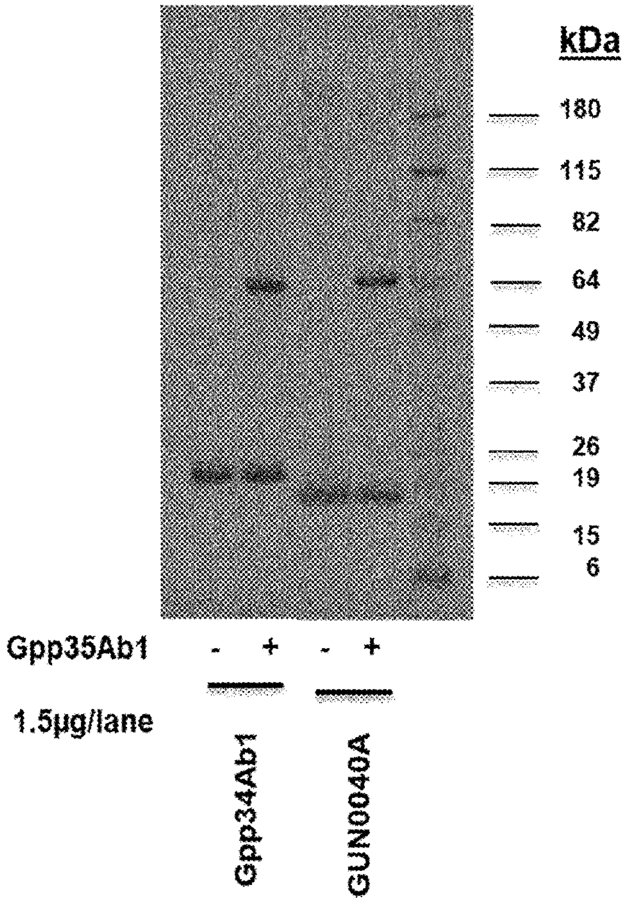
FIG. 3 is an image of SDS-PAGE analysis of purified proteins: Gpp34Ab1 alone (~20 kDa), Gpp34Ab1+ Gpp35Ab1 (bands at ~20 kDa for Gpp34Ab1 and ~65 kDa for Gpp35Ab1), GUN0040A alone (~17 kDa), and GUN0040A+Gpp35Ab1 (bands at ~17 kDa for GUN0040A and at ~65 kDa for Gpp35Ab1).

GUN0040A was identified from Gpp34Ab1. Gpp34Ab1 is active as a binary toxin requiring Gpp35Ab1 to display significant entomotoxicity against *D. virgifera*. The enhancing effect of Gpp35Ab1 on GUN0040A was tested using purified proteins and purified protein mix (FIG. 3).

Figure 4:
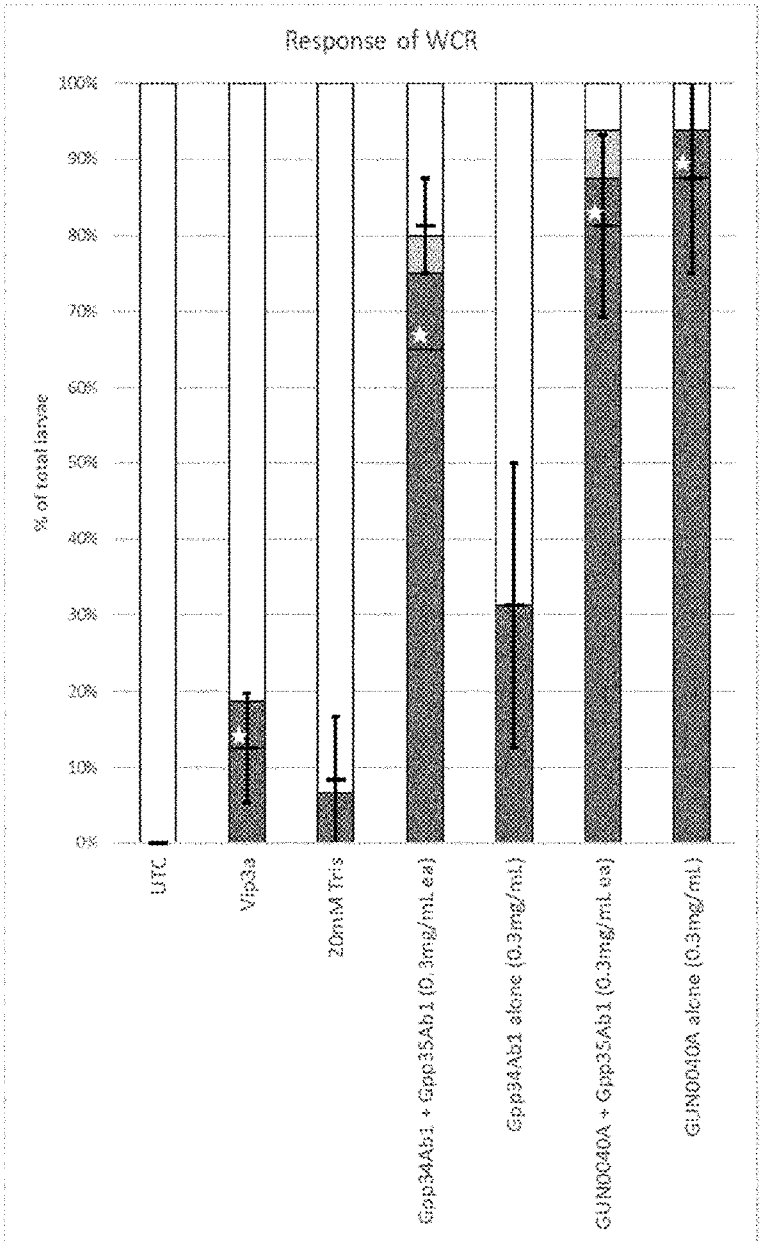
FIG. 4 is a graph depicting activity of purified protein: GUN0040A and Gpp34Ab1 with and without Gpp35Ab1 against WCRW. Gpp35Ab1 enhances the activity of Gpp34Ab1, but does not enhance the activity of GUN0040A. Untreated control (UTC) is a negative control only containing the insect diet, Vip3A is a negative control containing recombinant bacterial extract with Lepidopteran controlling toxin Vip3Aa19, and 20 mMTris is a negative control containing the buffer solution used for the purified proteins assays. Bars is % of mortality±SE

An aliquot (20 μL) of protein solution, at 0.3 mg/ml each, was applied to top of the diet (approximately 200 μl of WCRMO-1 diet/well of a standard 96-well microtiter plate), and subsequently dried in a laminar flow hood for approximately 30 minutes. Once dry, a single neonate WCRW larva was infested per well using a fine tipped watercolor brush. After larvae were infested, each plate was covered with a sealing film (Excel Scientific, Inc., Thermalseal RTS™, TSS-RTQ-100) and placed in a 25° C. dark growth chamber for 5 days. At day 5, each plate was removed from the growth chamber and larvae were assessed for mortality and stunted phenotypes (stunted depicted as the darkest shading with a star or slightly stunted depicted as the lightest shading; dead being depicted as the darkest shading with no star and unaffected being unshaded). Results surprisingly show no enhancing effect of Gpp35Ab1 on GUN0040A (FIG. 4) demonstrated that GUN0040A acts as a single protein toxin contrarily to Gpp34Ab1 that require Gpp35Ab1 to display significant control on coleopteran.

Example 5

In this Example, potency of purified GUN0040A protein expressed as $LC_{50}$, which represents the predicted protein concentration (μg/cm$^2$) that results in mortality of 50% of the infested insect larvae.

The first step of the $LC_{50}$ process was to determine the concentration range needed to kill approximately 50% and 100% of the insect larvae in bioassay. An aliquot (20 μL) of protein solution was applied to top of the diet (approximately 200 μL of WCRMO-1 diet/well of a standard 96-well microtiter plate), and subsequently dried in a laminar flow hood for approximately 30 minutes. Once dry, a single neonate WCRW larva was infested per well using a fine tipped watercolor brush. After larvae were infested, each plate was covered with a sealing film (Excel Scientific, Inc., Thermalseal RTS™, TSS-RTQ-100) and placed in a 25° C. dark growth chamber for 5 days. At day 5, each plate was removed from the growth chamber and larvae were assessed for mortality (alive or dead).

Once the appropriate protein concentration range was determined, 5 concentrations of the purified protein were tested in a dose-response artificial diet overlay bioassay. As described above the assays were incubated for 5 days and assessed for lethal and sublethal affects. JMP® 14.2.0 (1989-2021) software was used for the statistical data analysis. Probit analysis using the Generalized Linear Model for a Binomial distribution with a $\log_{10}$ transformation of the dose variable was used to analyze larval mortality (total dead larvae relative to total larvae tested) per protein concentration (Finney, 1971).

Figure 5A:
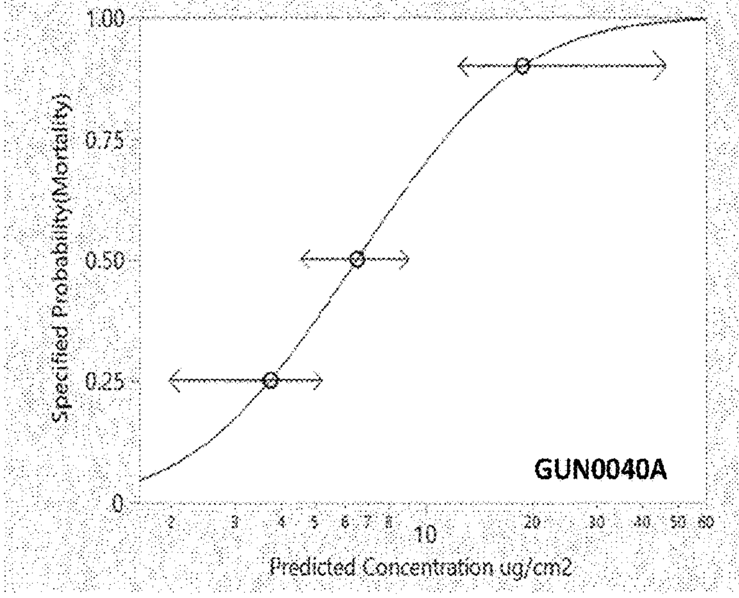
FIG. 5A is a graph of the probit analysis measuring $LC_{50}$ of GUN0040A.
Figure 5B:
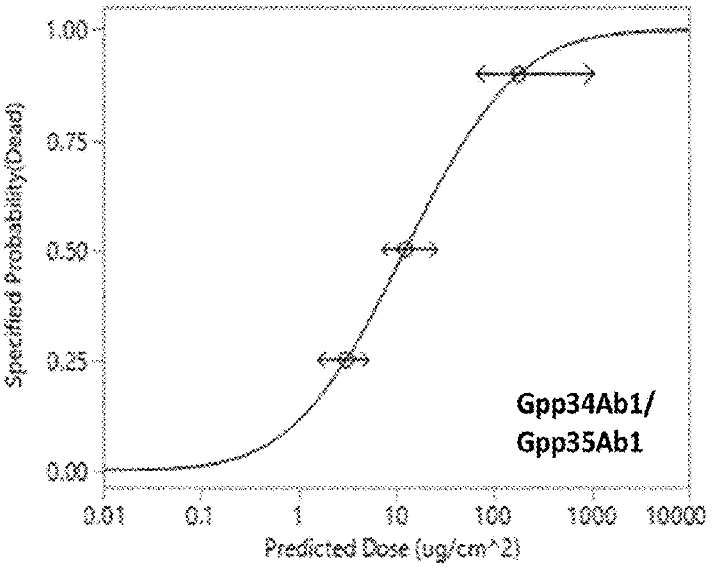
FIG. 5B is a graph of the probit analysis measuring $LC_{50}$ of Gpp34Ab1/Gpp35Ab1.

The predicted $LC_{50}$ of GUN0040A was 6.51 μg/cm$^2$ with 95% confidence interval of 4.45-9.05 μg/cm$^2$ for susceptible WCR (FIG. 5A) while the $LC_{50}$ or the reference binary toxin Gpp34Ab1/Gpp35Ab1 was 12.42 μg/cm$^2$ with 95% confidence interval of 7.17-26.39 μg/cm$^2$ for susceptible WCR (FIG. 5B).

Example 6

In this Example, GUN0040A was transiently expressed in *N. benthamiana.*

Figure 7C:
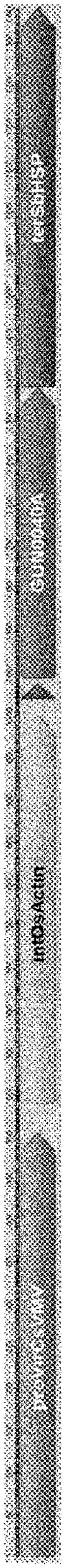

A synthetic *Nicotiana tabacum* codon-optimized sequence encoding GUN0040A plus an N-terminal Histidine TAG was cloned between the strong constitutive Sc4 promoter (Schanmann et al., 2003) or the CsVMV promoter (Verdaguer et al., 1996) linked to a rice actin 5' UTR, and a Sorghum HSP polyadenylation sequence present in a plant binary vector. The GUN0040A gene cassettes are represented by FIGS. 7B and 7C.

The resulting binary plasmids were transferred into the *Agrobacterium* strain GV3101 according to Komari et al. (1996) giving the strains 345 (proSc4::6×His::GUN0040A::SbHSP), and 358 (proCsVMV::intOsActin:: 6×His::GUN0040A::SbHSP). A standard *Nicotiana benthamiana* agro-infiltration protocol (essentially as described in bio-protocol.org) was used to transiently transform leaf sectors with the *agrobacterium* strain.

Figure 6A:
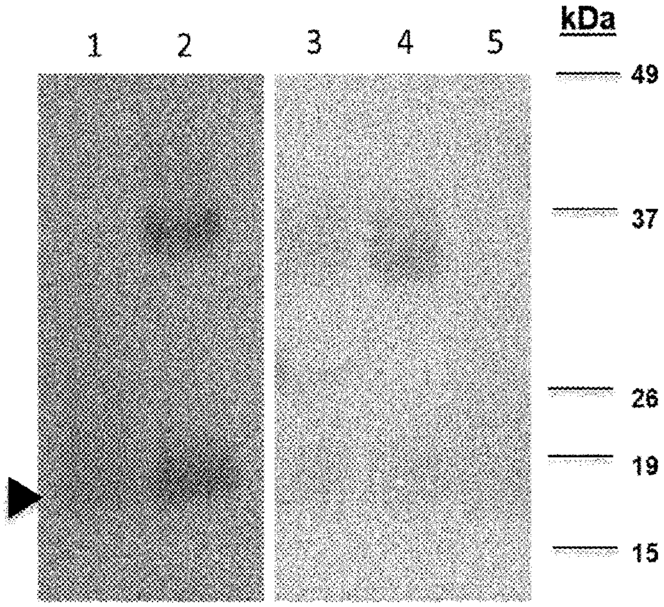
FIGS. 6A and 6B depict *Agrobacterium*-mediated transient expression of GUN0040A in *Nicotiana benthamiana* leaf tissue to determine phytotoxicity and efficacy.

Total proteins were extracted from transformed *N. benthamiana* leaves and expression of the protein(s) of interest was examined using Western blot analyses and a monoclonal antibody specific to the 6×His-Tag of the expressed recombinant protein as probe (FIG. 6A).

Figure 6B:
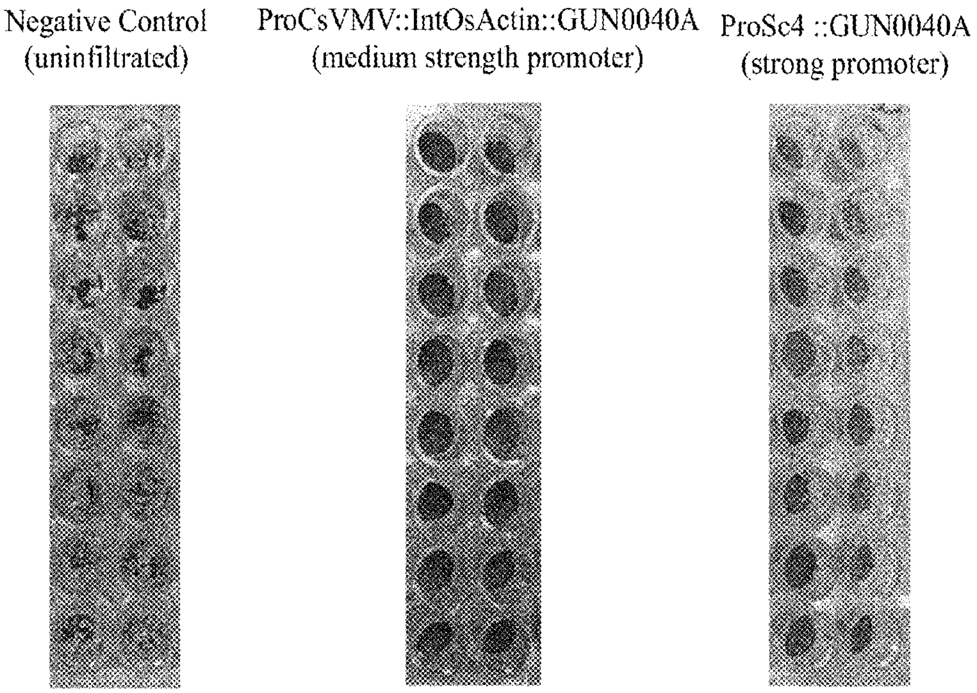

Leaf discs prepared from the agro-infiltrated portion of *N. benthamiana* leaves were used in Southern Corn Rootworm (SCRW) larval insect feeding assays (Table 2; FIG. 6B). The mortality and stunting (SCRW Efficacy, Table 2) of the larvae feeding on the agro-infiltrated leaf discs is rated using a scale from 1 (no feeding, high larval mortality) to 3 (little or no mortality, leaf disc consumed) five days after treatment.

TABLE 2

| Average Leaf Disc Consumption | | | | |
|---|---|---|---|---|
| Construct | Promoter Strength | ZsGreen/p19 | SCRW Efficacy | Expression Detected |
| proCsVMV::intOsActin::GUN0040A::terSbHSP | Medium | proSc4::p19::termVir35S_N2 | 1.15 | Yes |
| proSc4::GUN0040A:terSbHSP | High | proSc4::p19::termVir35S_N2 | 1.1 | Yes |
| Negative Control | High | proSc4::p19::termVir35S_N2 | 2.53 | Yes |

In addition, leaf discs prepared from the agro-infiltrated portion of *N. benthamiana* leaves were evaluated (Table 3) for phytotoxicity using a scale ranging from 1 (healthy tissue) to 4 (necrotic) 7 days post-infiltration.

TABLE 3

| Average Phytotoxicity Ratings | | | | |
|---|---|---|---|---|
| Construct | Promoter Strength | ZsGreen/p19 | Phytotox Score | Expression Detected |
| proCsVMV::intOsActin::GUN0040A::terSbHSP | Medium | proSc4::p19::termVir35S_N2 | 1.21 | Yes |
| proSc4::GUN0040A:terSbHSP | High | proSc4::p19::termVir35S_N2 | 1.17 | Yes |
| proCsVMV::intOsActin::CyclA2::terSbHSP Positive Control | Medium | proSc4::p19::termVir35S_N2 | 3.92 | Yes |

Example 7

The plant binary construct GCT-1125 was produced proVirCsVMV (Verdaguer et al. 1996), intOsActin (WO2020183022A1) and terSbHSP (WO2020183022A1) to drive expression of GUN0040A maize codon optimized sequence for production of GUN0040a protein (SEQ ID NO:1) in maize cells (Table 4).

The plant binary construct GCT-1126 was produced using the Brachypodium distachyon elongation factor 1-alpha promoter (proBdEF1) and 5'URE (intBdEF1) and t terSbHSP (WO2020183022A1) to drive expression of GUN0040A maize codon optimized sequence for production of GUN0040a protein (SEQ ID NO:1) in maize cells (Table 4).

The plant binary construct GCT-1127 was produced proAtNOS, intOsActin (WO2020183022A1) and terSbHSP (WO2020183022A1) to drive expression of GUN0040A maize codon optimized sequence for production of GUN0040a protein (SEQ ID NO:1) in maize cells (Table 4).

Each of the GCT-1125, GCT-1126 and GCT-1127 were individually transformed into the maize inbred B104 essentially as described by Frame et al. (2006). A minimum of 10 individuals, single copy transformants with intact T-DNAs, were produced for each construct. QRT-PCR and Western analyses were performed on T0 leaf material to select transgenic plant showing GUN0040A expression.

TABLE 4

| T-DNA structures used for stable plant transformation. | |
|---|---|
| Construct | T-DNA |
| GCT-1125 | [RB]-[proVirCsVMV::intOsActin::GUN0040A::terSbHSP]-[proTaHMWG::synZsGreen::terAtNOS]-[proBdUbi10::intBdUbi10::AfPAT::terVir35S_N2]-[LB] |
| GCT-1126 | [RB]-[proBdEF1::intBdEF1::GUN0040A::terSbHSP]-[proTaHMWG::synZsGreen:terAtNOS]-[proBdUbi10:intBdUbi10::AfPAT::terVir35S_N2]-[LB] |
| GCT-1127 | [RB]-[proAtNos::intOsActin::GUN0040A::terSbHSP]-[proTaHMWG::synZsGreen::terAtNOS]-[proBdUbi10::intBdUbi10::AfPAT::terVir35S_N2]-[LB] |

The selected transgenic plants and their progenies from constructs GCT-1125, GCT-1126 and GCT-1127 were gown in greenhouse condition.

Western corn rootworm, *Diabrotica virgifera virgifera* LeConte (WCRW) efficacy is tested in the greenhouse using a method of artificial infestation of eggs into the plant and then rating the roots after the eggs have hatched and the larvae have fed. WCRW efficacy assays are deployed in a randomized complete block design of 4 replicates of 3 infested plants. Negative (non-transgenic) and positive (transgenic plants expressing reference toxins) controls are utilized as comparators in the root damage assessment. Seeds are counted out and planted into 32 cell flats and placed in a greenhouse bay for germination. The greenhouse bays are set for corn growth with day temperature set to 26-29° C. at 50% RH and 17-20° C. at 50% RH at night. The light to dark ratio is 16:8. The seedlings are transplanted into 1 gallon pots at V2 (approximately 14 days). The plants are allowed to acclimate for approximately 2 days and then are infested with WCRW eggs. The eggs are delivered in a 0.16% agar solution at a rate of 800 eggs per ml. Each plant receives 2 ml of egg/agar solution. The solution is delivered in a 1 ml aliquot through a syringe or repeater pipette into each of 2 holes on either side of the plant, approximately 2 inches from the base of the plant and 2 inches deep. The eggs hatch after infestation in approximately 12 days. Once hatched the larvae feed for approximately 17-21 days. Plants are checked throughout the feeding cycle to monitor feeding progress and proper time to rate. When the plants are determined to be ready, the plants are removed from the greenhouse and washed and rated in our root processing area of the greenhouse complex. The roots are rated using the Iowa State NIS corn injury scale (Oleson et al. 2005). Analysis of variance is run at the event level comparing the negative to the negative and positive controls with Tukey pairwise comparisons for mean separation.

In view of the above, it will be seen that the several advantages of the disclosure are achieved and other advantageous results attained. As various changes could be made in the above methods without departing from the scope of the disclosure, it is intended that all matter contained in the above description and shown in the accompanying drawings shall be interpreted as illustrative and not in a limiting sense.

When introducing elements of the present disclosure or the various versions, embodiment(s) or aspects thereof, the articles “a”, “an”, “the” and “said” are intended to mean that there are one or more of the elements. The terms “comprising”, “including” and “having” are intended to be inclusive and mean that there may be additional elements other than the listed elements.

REFERENCES

Frame, B. R., McMurray, J. M., Fonger, T. M., Main, M. L., Taylor, K. W., Torney, F. J., Paz, M. M., and Wang, K. (2006). Improved *Agrobacterium*-mediated transformation of three maize inbred lines using M S salts. Plant Cell Rep 25: 1024-1034.

Huynh M P, Meihls L N, Hibbard B E, Lapointe S L, Niedz R P, Ludwick D C, et al. (2017) Diet improvement for western corn rootworm (Coleoptera: Chrysomelidae) larvae. PLoS ONE 12 (11): e0187997.

Moar W., Khajuria C., Pleau M., Ilagan O., Chen M., Jiang C., Price P., McNulty B., Clark T., Head G. (2017) Cry3Bb1-Resistant Western Corn Rootworm, *Diabrotica virgifera virgifera* (LeConte) Does Not Exhibit Cross-Resistance to DvSnf7 dsRNA, PLOS ONE 12(1)

Pleau, Huesing, Head, Feir (2002) Development of an artificial diet for the western corn rootworm, Entomologia Experimentalis et Applicata, Volume 105, Issue 1, Pages 1-11

Finney, D. J. (1971) Probit Analysis. 3rd Edition, Cambridge University Press, Cambridge.

Schünmann PHD, Llewellyn D J, Surin B, Boevink P, Feyter R C, Waterhouse, P M. (2003). A suite of novel promoters and terminators for plant biotechnology. Funct Plant Biol. 30:433-452.

Verdaguer B, de Kochko A, Beachy R N, Fauquet C. (1996). Isolation and expression in transgenic tobacco and rice plants, of the cassava vein mosaic virus (CVMV) promoter. Plant Mol Biol. 31:1129-39

Komari T, Hiei Y, Saito Y, Murai N, Kumashiro T. (1996). Vectors carrying two separate T-DNAs for co-transformation of higher plants mediated by *Agrobacterium tumefaciens* and segregation of transformants free from selection markers. Plant J. 10:165-74.

Verdaguer B, de Kochko A, Beachy R N, Fauquet C. (1996). Isolation and expression in transgenic tobacco and rice plants, of the cassava vein mosaic virus (CVMV) promoter. Plant Mol Biol. 31:1129-39.

Oleson J D, Park Y L, Nowatzki T M, Tollefson J J. Node-injury scale to evaluate root injury by corn rootworms (Coleoptera: Chrysomelidae). J Econ Entomol. 2005 February; 98(1):1-8. doi: 10.1093/jee/98.1.1. PMID: 15765660.

The invention claimed is:

1. A method of protecting a plant from infection by a plant pest, the method comprising: introducing into the plant a nucleic acid molecule encoding a polypeptide having at least 97% sequence identity to SEQ ID NO:1, wherein the plant expresses the nucleic acid molecule and wherein the polypeptide has pesticidal activity against one or more coleopteran pests selected from western corn rootworm (*Diabrotica virgifera virgifera*) and southern corn rootworm (*Diabrotica undecimpunctata howardi*), and wherein the plant is selected from the group consisting of tobacco, cotton, soybean, sunflower, rapeseed, wheat, maize, rice, barley, and sorghum.

2. A transformed plant, plant tissue, plant cell, or plant seed comprising a recombinant nucleic acid molecule encoding a polypeptide having at least 97% sequence identity to SEQ ID NO:1 stably incorporated into the plant genome, wherein the plant, plant tissue, plant cell, or plant seed is capable of expressing the recombinant nucleic acid molecule, wherein the polypeptide has pesticidal activity against one or more coleopteran pests selected from western corn rootworm (*Diabrotica virgifera virgifera*) and southern corn rootworm (*Diabrotica undecimpunctata howardi*), and wherein the plant, plant tissue, plant cell, or plant seed is selected from the group consisting of tobacco, cotton, soybean, sunflower, rapeseed, wheat, maize, rice, barley, and sorghum.

3. A recombinant nucleic acid molecule comprising a nucleotide sequence encoding a polypeptide having at least 97% sequence identity to SEQ ID NO:1, wherein the polypeptide has pesticidal activity against one or more coleopteran pests selected from western corn rootworm (*Diabrotica virgifera virgifera*) and southern corn rootworm (*Diabrotica undecimpunctata howardi*), and wherein the nucleotide sequence encoding the polypeptide is operably linked to a promoter capable of driving expression of the nucleotide sequence in a plant or a plant cell, wherein the plant or plant cell is selected from the group consisting of tobacco, cotton, soybean, sunflower, rapeseed, wheat, maize, rice, barley, and sorghum.

4. A vector comprising a recombinant nucleic acid molecule comprising a nucleotide sequence encoding a polypeptide having at least 97% sequence identity to SEQ ID NO:1, wherein the polypeptide has pesticidal activity against one or more coleopteran pests selected from western corn rootworm (*Diabrotica virgifera virgifera*) and southern corn rootworm (*Diabrotica undecimpunctata howardi*), and wherein the nucleotide sequence encoding the polypeptide is operably linked to a promoter capable of driving expression of the nucleotide sequence in a plant or a plant cell, wherein the plant or plant cell is selected from the group consisting of tobacco, cotton, soybean, sunflower, rapeseed, wheat, maize, rice, barley, and sorghum.

5. A transformed host cell comprising a recombinant nucleic acid molecule comprising a nucleotide sequence encoding a polypeptide having at least 97% sequence identity to SEQ ID NO:1, wherein the polypeptide has pesticidal activity against one or more coleopteran pests selected from western corn rootworm (*Diabrotica virgifera virgifera*) and southern corn rootworm (*Diabrotica undecimpunctata howardi*), and wherein the nucleotide sequence encoding the polypeptide is operably linked to a promoter capable of driving expression of the nucleotide sequence in a plant or a plant cell, wherein the plant or plant cell is selected from the group consisting of tobacco, cotton, soybean, sunflower, rapeseed, wheat. maize, rice, barley, and sorghum.

6. The method of claim 1, wherein the polypeptide consists of the amino acid sequence of SEQ ID NO: 1.

7. The transformed plant, plant tissue, plant cell, or plant seed of claim 2, wherein the polypeptide consists of the amino acid sequence of SEQ ID NO: 1.

8. The recombinant nucleic acid molecule of claim 3, wherein the polypeptide consists of the amino acid sequence of SEQ ID NO: 1.

9. The vector of claim 4, wherein the polypeptide consists of the amino acid sequence of SEQ ID NO: 1.

10. The transformed host cell of claim 5, wherein the polypeptide consists of the amino acid sequence of SEQ ID NO: 1.

* * * * *

SEQUENCE LISTING

```
Sequence total quantity: 2
SEQ ID NO: 1            moltype = AA  length = 114
FEATURE                 Location/Qualifiers
source                  1..114
                        mol_type = protein
                        organism = Bacillus thuringiensis
SEQUENCE: 1
MSAREVHITV INVSSFELQL ESKTYLNHGE WILTPTNVPE GGNLNFRADS DGFATGAEGS  60
IFYTVPDGEI KLYFDDPYVG SNAFAATTSS PSVSVQAVGS SGNVCKVMYV ITNK        114

SEQ ID NO: 2            moltype = AA  length = 119
FEATURE                 Location/Qualifiers
source                  1..119
                        mol_type = protein
                        organism = Bacillus thuringiensis
SEQUENCE: 2
MSAREVHIEI NNKTRHTLQL EDKTKLSGGR WRTSPTNVAR DTIKTFVAES HGFMTGVEGI  60
IYFSVNGDAE ISLHFDNPYI GSNKCDGSSD KPEYEVITQS GSGDKSHVTY TIQTVSLRL   119
```